US009004916B2

(12) United States Patent
Ruiz-Vela et al.

(10) Patent No.: US 9,004,916 B2
(45) Date of Patent: Apr. 14, 2015

(54) ORTHODONTIC BRACKET AND METHOD OF CORRECTING MALPOSITIONED TEETH

(75) Inventors: Albert Ruiz-Vela, Alta Loma, CA (US); Farrokh Farzin-Nia, Inglewood, CA (US); Ronald J. Sirney, Alta Loma, CA (US); Todd I. Oda, Torrance, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 12/689,145

(22) Filed: Jan. 18, 2010

(65) Prior Publication Data

US 2010/0261131 A1 Oct. 14, 2010

Related U.S. Application Data

(60) Provisional application No. 61/145,345, filed on Jan. 16, 2009.

(51) Int. Cl.
*A61C 3/00* (2006.01)
*A61C 7/28* (2006.01)

(52) U.S. Cl.
CPC ...................... *A61C 7/287* (2013.01)

(58) Field of Classification Search
USPC ............................ 433/2, 8–17, 229
See application file for complete search history.

(56) References Cited

U.S. PATENT DOCUMENTS

| | | | | |
|---|---|---|---|---|
| 2,549,528 A | * | 4/1951 | Russell | ............................ 433/13 |
| 4,197,642 A | | 4/1980 | Wallshein | |
| 4,248,588 A | | 2/1981 | Hanson | |
| 4,492,573 A | | 1/1985 | Hanson | |
| 4,712,999 A | * | 12/1987 | Rosenberg | ........................ 433/8 |
| 5,161,969 A | * | 11/1992 | Pospisil et al. | ..................... 433/8 |
| 5,224,858 A | | 7/1993 | Hanson | |
| 5,322,435 A | * | 6/1994 | Pletcher | ......................... 433/11 |
| 5,586,882 A | | 12/1996 | Hanson | |
| 5,630,715 A | | 5/1997 | Voudouris | |
| 5,908,293 A | | 6/1999 | Voudouris | |
| 6,071,118 A | | 6/2000 | Damon | |
| 6,168,428 B1 | * | 1/2001 | Voudouris | ...................... 433/11 |
| 6,193,508 B1 | | 2/2001 | Georgakis | |

(Continued)

FOREIGN PATENT DOCUMENTS

EP    1428483 A2    6/2004

OTHER PUBLICATIONS

Search Report and Written Opinion in counterpart Application No. PCT/US2010/021327, mailed Mar. 24, 2010.

(Continued)

*Primary Examiner* — Heidi M Eide
*Assistant Examiner* — Matthew Saunders
(74) *Attorney, Agent, or Firm* — Wood, Herron & Evans, LLP

(57) ABSTRACT

An orthodontic bracket includes a bracket body and a ligating member. The ligating member retains an archwire in an archwire slot and includes archwire control structure including projecting portions spaced apart in a mesial-distal direction with a recessed area therebetween. The recessed area and the projecting portions overlie the archwire slot. The recessed area may include a flat or a curved surface in a mesial-distal direction. The recessed area and projecting portions may define a radius of curvature that is less than the radius of curvature of the archwire seated in the slot. The archwire contacts one or both of the projecting portions resulting in a larger moment arm and better rotational control of the bracket with the force applied by the archwire.

11 Claims, 11 Drawing Sheets

(56) References Cited

U.S. PATENT DOCUMENTS

| | | | |
|---|---|---|---|
| 6,368,105 B1* | 4/2002 | Voudouris et al. | 433/11 |
| 6,607,383 B2 | 8/2003 | Abels et al. | |
| 6,776,613 B2 | 8/2004 | Orikasa | |
| 6,843,651 B2* | 1/2005 | Orikasa | 433/13 |
| 6,932,597 B2 | 8/2005 | Abels et al. | |
| 6,939,133 B2 | 9/2005 | Voudouris | |
| 6,942,483 B2 | 9/2005 | Heiser | |
| 6,960,080 B2 | 11/2005 | Abels et al. | |
| 7,033,170 B2 | 4/2006 | Cordato | |
| 7,134,873 B2 | 11/2006 | Miyaji et al. | |
| 7,204,690 B2 | 4/2007 | Hanson | |
| 7,234,935 B2 | 6/2007 | Abels et al. | |
| 7,255,557 B2 | 8/2007 | Forster | |
| 7,267,545 B2* | 9/2007 | Oda | 433/10 |
| 7,335,020 B2* | 2/2008 | Castner et al. | 433/11 |
| 7,442,039 B2 | 10/2008 | Opin et al. | |
| 2005/0239012 A1* | 10/2005 | Bathen et al. | 433/10 |
| 2006/0154196 A1* | 7/2006 | Oda | 433/13 |
| 2006/0177790 A1* | 8/2006 | Farzin-Nia et al. | 433/10 |
| 2006/0228662 A1 | 10/2006 | Lokar et al. | |
| 2007/0248928 A1* | 10/2007 | Damon | 433/10 |
| 2007/0275342 A1* | 11/2007 | Oda | 433/10 |
| 2008/0113311 A1* | 5/2008 | Forster | 433/11 |
| 2009/0004617 A1 | 1/2009 | Oda et al. | |
| 2009/0004619 A1* | 1/2009 | Oda et al. | 433/24 |
| 2009/0061376 A1 | 3/2009 | Wool | |
| 2009/0075227 A1 | 3/2009 | Opin et al. | |
| 2009/0155734 A1* | 6/2009 | Damon | 433/10 |
| 2009/0325120 A1* | 12/2009 | Lewis et al. | 433/13 |

OTHER PUBLICATIONS

Japanese Patent Office, English translation of Office Action in Japanese Patent Application No. 2011-546416, dated Dec. 3, 2013 (4 pages).

Chinese Patent Office, Office Action in Chinese Patent Application No. 2010080011140.9, dated Jul. 22, 2013.

* cited by examiner

ORTHODONTIC BRACKET AND METHOD OF CORRECTING MALPOSITIONED TEETH

CROSS-REFERENCE TO RELATED APPLICATION

This application claims the benefit of the filing date of U.S. Patent Application Ser. No. 61/145,345 entitled "ORTHODONTIC BRACKET AND METHOD OF CORRECTING MALPOSITIONED TEETH," filed on Jan. 16, 2009, the disclosure of which is incorporated by reference herein in its entirety.

BACKGROUND

Orthodontic treatment involves the application of mechanical forces to urge improperly positioned teeth into correct alignment. One form of orthodontic treatment includes the use of orthodontic brackets respectively fixed to individual teeth either by bands or, more commonly, fixed into place with adhesive. After the brackets are fixed to the teeth of the upper or lower arch, a resilient archwire is then seated in the archwire slots of the upper or lower brackets. The upper and/or lower teeth may be treated in this manner. The archwire(s) may then be secured in place with respect to each bracket by individual ligature wires or elastic bands. This results in active ligation or, in other words, ligation that forces the archwire to the base surface of the archwire slot.

Alternative bracket designs ligate the archwire into position by a movable closure member or cover. Such movable closure members may be permanently, but movably, coupled with the bracket body or may be a separate element non-permanently coupled with the bracket body. These types of archwire slot closure members may ligate the archwire either passively or actively. In passive designs, the closure member does not force the archwire to the base surface of the archwire slot but, instead, allows the archwire, or at least a portion thereof, to be spaced from the base of the archwire slot or from the movable closure member. In contrast, in active ligation, the movable closure member or other ligating element forces the archwire to the base surface of the archwire slot. The movable closure member is opened for inserting the archwire into the slot and then closed for retaining the archwire in the archwire slot. This movable closure member includes, but is not limited to, a ligating slide, a clip, an elastic or resilient cover, etc. Correction occurs as the archwire aligns the teeth to the shape of the archwire.

There is a need for an orthodontic bracket that provides consistent rotational control of the tooth and an improved method for controlling rotation of the tooth during treatment.

SUMMARY OF THE INVENTION

In one aspect, an orthodontic bracket is provided comprising a bracket body adapted to be secured to a tooth. The bracket body includes a mesial end, a distal end, a lingual side, a labial side, and an archwire slot extending generally in a mesial-distal direction. The archwire slot includes a base surface, opposing side walls extending in a labial direction from the base surface and an opening on the labial side opposite the base surface for receiving an archwire. The bracket further comprises a closure member movable between an open position and a closed position. The closure member is coupled to the bracket body in the closed position to retain the archwire in the archwire slot. The closure member includes a lingual side with archwire control structure including first and second projecting portions spaced apart in a mesial-distal direction and a recessed area therebetween. The recessed area and the first and second projecting portions overlie the archwire slot when the closure member is in the closed position, with first projecting portion being proximate the mesial end of the archwire slot and the second projecting portion being proximate the distal end of the archwire slot when the closure member is in the closed position, and at least one of the first or second projecting portions is adapted to contact the archwire when the closure member is in the closed position.

The closure member may further comprise various structures such as a slide member, a clip, a resilient closure, a pivoting member, etc. The recessed area and the first and second projecting portions may also take many forms. As examples, these elements of the closure member may generally form a generally rectangular cross sectional shape when viewed in an occlusal-gingival direction. Optionally, the recessed area may include a flat surface or a surface curved in a mesial-distal direction. The recessed surface and first and second projecting portions together define a radius of curvature that is less than the radius of curvature of the archwire portion that is seated in the associated slot of that bracket. This will ensure that the archwire contacts the first and/or second projecting portions instead of the recessed surface thereby resulting in a larger moment arm and better rotational control of the bracket with the force applied by the archwire.

More specifically, the lingual side or surface of the closure member can include a recess overlying the archwire slot when the closure member is in the closed position and the recess can have mesial and distal edges. At least one of the mesial edge or distal edge is adapted to contact the archwire when the closure member is in the closed position.

In another embodiment, the recessed area is defined by a mesial side wall, a distal side wall, and a surface therebetween. The surface is configured such that the archwire does not contact the surface when the clip is in the closed position and when the archwire is in contact with one or both of the mesial and distal projecting portions.

In another aspect, an orthodontic bracket is provided comprising a bracket body adapted to be secured to a tooth and a clip movable between an open position and a closed position. The bracket body includes a mesial end, a distal end, a lingual side, a labial side, an occlusal side, a gingival side, an occlusal-gingival slot extending generally from the occlusal side to the gingival side, and an archwire slot extending generally from the mesial end to the distal end. The archwire slot includes a base surface, opposing side walls extending in a labial direction from the base surface, and an opening on the labial side opposite the base surface for receiving an archwire.

The clip is coupled to the bracket body in the closed position to retain the archwire in the archwire slot. The clip includes a lingual leg and a labial leg connected by a lateral section and has a generally U-shaped cross section. The lingual leg is configured to slidably cooperate with the occlusal-gingival slot. The labial leg has a lingual side with archwire control structure that includes mesial and distal projecting portions having a recessed area therebetween. The archwire control structure overlies the archwire slot when the clip is in the closed position and at least one of the mesial and distal projecting portions is adapted to contact the archwire when the clip is in the closed position. In one embodiment, the clip is bifurcated.

In another embodiment, an orthodontic member is provided for use with an orthodontic bracket that is adapted to be secured to a tooth. The bracket includes a mesial end, a distal end, a lingual side, a labial side, an occlusal side, and a gingival side. The bracket further includes a tiewing and an archwire slot that extends generally from the mesial end to the distal end. The archwire slot includes a base surface and gingival and occlusal side walls that extend in a labial direction from the base surface, and an opening on the labial side opposite the base surface that receives an archwire therein.

The member includes a main body that is configured to cover at least a portion of the bracket when the orthodontic member is coupled to the bracket. The main body has labial and lingual surface. The lingual surface includes archwire control structure. The archwire control structure includes mesial and distal projecting portions separated by a recessed area. The member further includes an engaging member that extends from the main body and that is configured to engage the tie wing to removably couple the orthodontic member to the bracket. When the archwire is positioned in the archwire slot and the orthodontic member is coupled to the bracket, the mesial and distal projecting portions overlie the archwire slot and are adapted to contact the archwire.

A method of correcting malpositioned teeth according to the invention can comprise applying a plurality of orthodontic brackets constructed in one or more of the manners discussed herein to the teeth of a patient. An archwire is then retained in the respective archwire slots of the orthodontic brackets with the ligating members coupled to the bracket such that the archwire contacts at least one of the first or second projecting portions or at least one of the mesial or distal edges, and without contacting another area of the ligating member.

BRIEF DESCRIPTION OF THE DRAWINGS

The accompanying drawings, which are incorporated in and constitute a part of this specification, illustrate embodiments of the invention and, with the general description given above, together with the detailed description given below, serve to explain various aspects of the invention.

DETAILED DESCRIPTION

Figure 1:
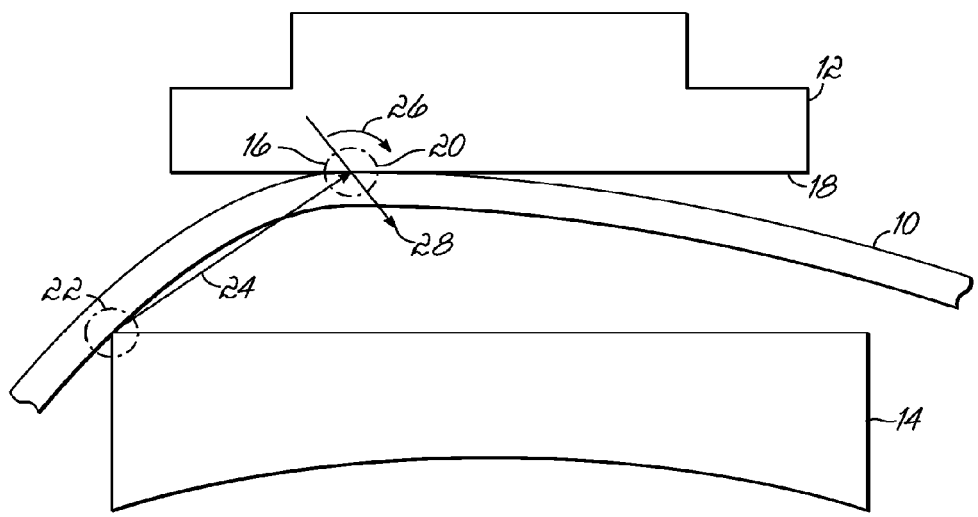
FIG. 1 is a schematic, cross-sectional view of a bracket body, closure member, and archwire of a conventional bracket and archwire assembly.

Referring to FIG. 1, the manner in which a ligated archwire 10 engages with a typical movable cover or closure member 12 of an orthodontic bracket 14 is depicted. As shown, the archwire 10 is passively ligated. That is, the archwire 10 is not secured to either of the closure member 12 or the bracket 14 and may, consequently, move or bend during treatment. Due to its radius of curvature, especially along anterior teeth, the archwire 10 can develop a point contact 16 with the underside or lingual side 18 of the closure member 12 at the apex 20 of its curvature. Where the archwire 10 also contacts the bracket 14 at the mesial or distal portions of the archwire slot (shown at 22), a moment arm 24 is formed.

The moment arm 24 allows application of torque 26 to the tooth (not shown) due to the force 28 generated by the archwire 10 contact on the closure member 12 at 16 and on the bracket 14 at 22. The torque 26 causes the bracket 14, and therefore the tooth, to rotate into a predetermined position. Unfortunately, this point contact 16 provides minimal control of bracket rotation since the apex 20, and thus the point contact 16, can easily shift or move along the lingual side 18 of the closure member 12 during treatment. Consequently, as the apex 20 moves, the moment arm 24 changes length. This in turn causes problems controlling tooth rotation because the torque 26 may change in an unpredictable manner. The practitioner, therefore, has less control over the movement of the tooth. It will be appreciated that a lack of control or limited control of tooth rotation may lead to extended treatment time.

Figure 2:
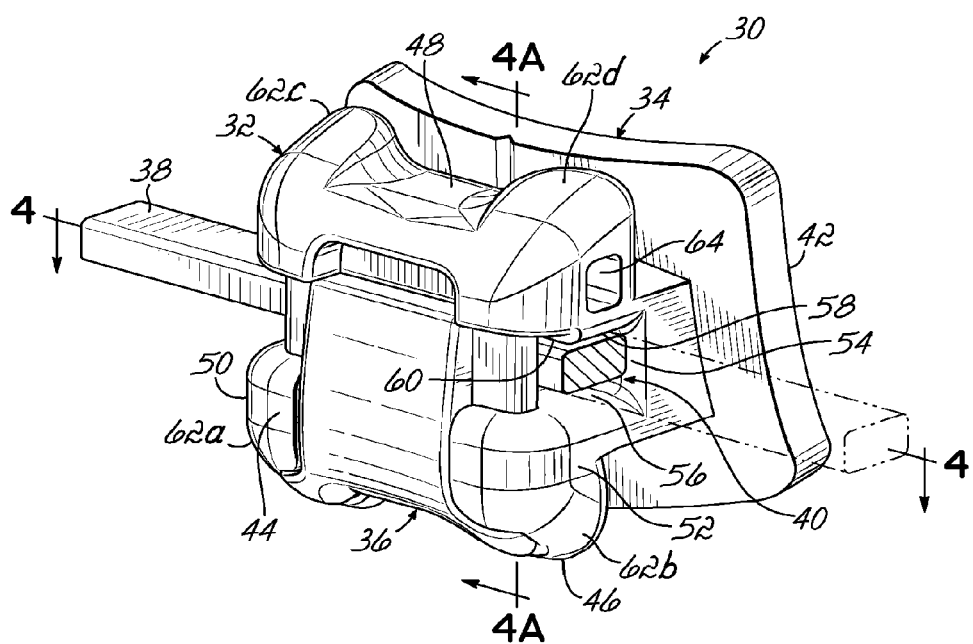
FIG. 2 is a perspective view of an orthodontic bracket holding an archwire in accordance with one embodiment of the invention.
Figure 3:
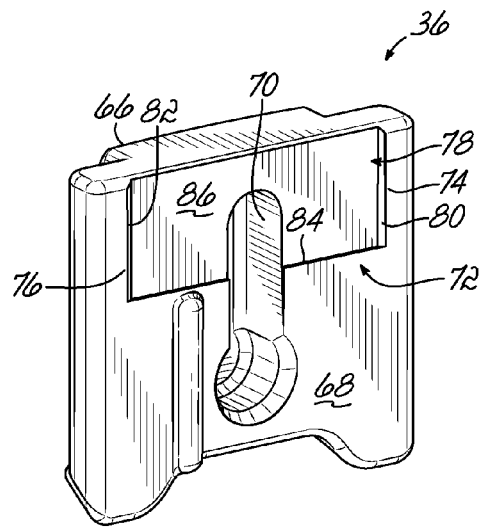
FIG. 3 is a perspective view of a closure member in the illustrative form of a slide, as used in the orthodontic bracket shown in FIG. 2.

With reference FIGS. 2 and 3, in one exemplary embodiment, an orthodontic bracket 30 includes a bracket body 32 configured to be mounted to a tooth (not shown) using any suitable base structure 34 and a suitable ligating or closure member 36, which in this illustration, is a slide member for captivating an archwire 38 within an archwire slot 40. The closure member 36 is coupled to the bracket body 32 and in the closed position, retains the archwire 38 in the archwire slot 40.

According to embodiments of the invention, the closure member 36 is designed with archwire control structure 72, described below, that provides predictable, consistent contact between the archwire 38 and the orthodontic bracket 30. In this regard, the archwire control structure limits contact between the archwire 38 and the closure member 36 to specific locations. Further, the specific locations may be predetermined and during treatment may not shift. By way of example, the archwire control structure may provide two-point contact between the orthodontic bracket 30 and the archwire 38. The archwire 38 may contact both the bracket body 32 and the closure member 36. In another configuration, two-point contact may occur at two locations on the closure member 36. In one exemplary embodiment, the archwire control structure limits contact between the archwire 38 and the closure member 36 to one or two predetermined locations. In addition, three- and four-point contact between the archwire 38 and the orthodontic bracket 30 is also contemplated.

To that end, the orthodontic bracket 30, unless otherwise indicated, is described herein using a reference frame with the orthodontic bracket 30 attached to a labial surface of a tooth on the upper jaw. Consequently, as used herein, terms such as labial, lingual, mesial, distal, occlusal, and gingival used to describe the bracket 30 are relative to the chosen reference frame. The embodiments of the invention, however, are not limited to the chosen reference frame and descriptive terms, as the orthodontic bracket 30 may be used on other teeth and in other orientations within the oral cavity. For example, the bracket 30 may also be located on an anterior tooth in the lower jaw or maxilla and be within the scope of the invention. Those of ordinary skill in the art will recognize that the descriptive terms used herein may not directly apply when there is a change in reference frame. Nevertheless, the invention is intended to be independent of location and orientation within the oral cavity and the relative terms used to describe embodiments of the invention are to merely provide a clear description in conjunction with the drawings. As such, the relative terms labial, lingual, mesial, distal, occlusal, and gingival in no way limit the invention to a particular location or orientation.

Accordingly, and with reference to the bracket body 32 shown in FIG. 2, when the bracket body 32 is mounted to the labial surface of a tooth carried on the patient's upper jaw, the bracket body 32 has a lingual side 42, a labial side 44, an occlusal side 46, a gingival side 48, a mesial end 50, and a distal end 52. The archwire slot 40 extends generally in a mesial-distal direction, such as from the mesial end 50 to the distal end 52. The archwire slot 40 includes a base surface 54, opposing side walls 56, 58 extending in a labial direction from the base surface 54 and an opening 60 on the labial side 44 opposite the base surface 54 for receiving the archwire 38. The lingual side 42 of the bracket body 32 is configured to be secured to a tooth in any conventional manner, including for example, by an appropriate orthodontic cement or adhesive or by a band around an adjacent tooth (not shown).

The bracket body 32 may further include one or more tie wings. As shown best in FIG. 2, in one embodiment, the bracket body 32 may be formed with two occlusal tie wings 62a, 62b projecting from the occlusal side 46 and two gingival tie wings 62c, 62d projecting from the gingival side 48. The tie wings 62a-62d permit coupling of other orthodontic elements such as, ligatures, power chains, among others, to the bracket body 32. While tie wings are shown and described, embodiments of the invention are not so limited, as it will be appreciated that embodiments of the invention may or may not have one or more tie wings 62a-62d.

Additionally, as shown in FIG. 2, the bracket body 32 may further include a horizontal slot 64 generally aligned parallel to the archwire slot 40 and configured for receiving temporary attachment devices, for example, a removable hook (not shown). The horizontal slot 64 may extend from the mesial end 50 to the distal end 52 of the bracket body 32 to form one continuous horizontal slot.

With reference to FIGS. 2 and 3, the closure member 36 has a labial surface 66 and a lingual surface 68. As shown in FIG. 3, the lingual surface 68 of closure member 36 includes a retaining slot 70 that extends generally in the gingival-occlusal direction (e.g., in the direction of movement of closure member 36). A spring pin (not shown) in the bracket body 32 is received in retaining slot 70. Additional details of the retaining slot 70 and spring pin can be found in co-owned U.S. application Ser. No. 12/147,877, the disclosure of which is incorporated by reference herein in its entirety. The closure member 36 may, therefore, be slid from an open position to a closed position without unintentional removal of the closure member 36 from bracket body 32. However, other means for retaining the closure member 36 are known in the art and, as such, embodiments of the invention are not limited to those having a retaining slot/spring pin securing mechanism.

With reference to FIG. 3, in one embodiment, the lingual surface 68 of the closure member 36 is designed with archwire control structure, generally designated 72. In the embodiment depicted in FIGS. 3 and 4A, the archwire control structure 72 may include mesial and distal projecting portions 74, 76 or edges spaced apart in a mesial-distal direction with a recess or a recessed area 78 therebetween. The recessed area 78 may be defined by mesial, distal, and occlusal side walls 80, 82, 84 to define a rectangular shaped recessed area 78. The recessed area 78 may also be defined by a recessed surface 86 that is inset or recessed into the lingual surface 68 or offset in the labial direction from the lingual surface 68. Thus, the recessed area 78 may be a blind recessed area in the lingual surface 68 of the closure member 36. However, the recessed area 78 may include a through-hole, cutout, or opening that extends through the closure member 36 from the lingual surface 68 to the labial surface 66 thereof.

Figure 4B:
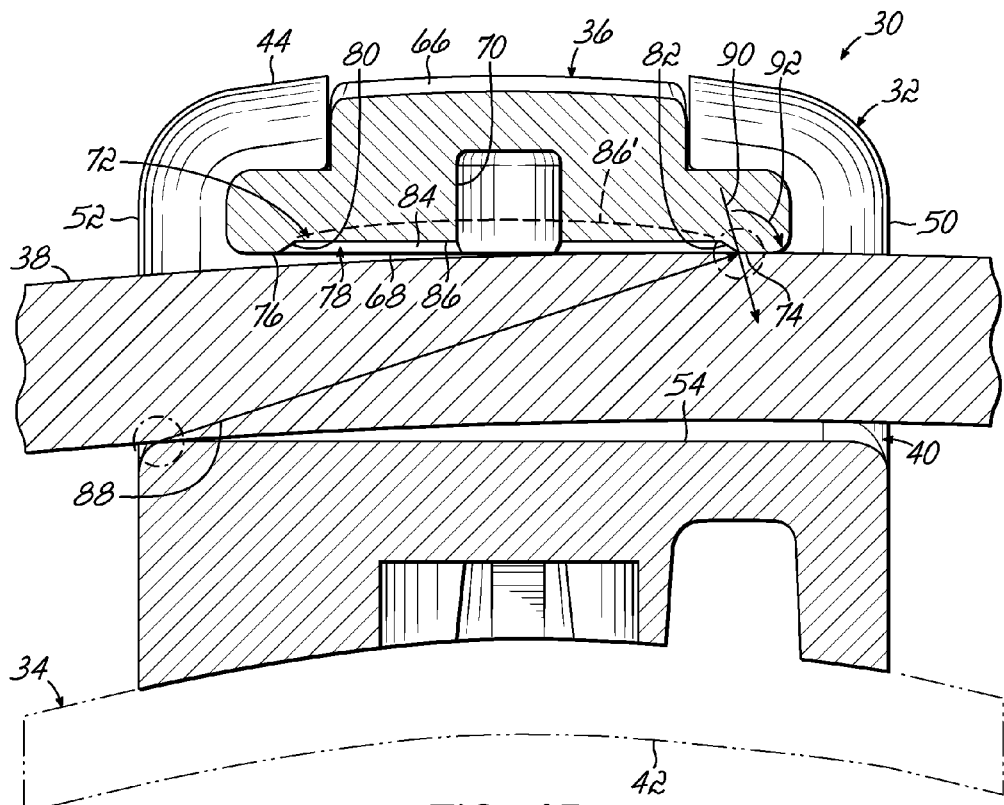
FIG. 4B is a cross-sectional view taken along section line 4-4 of FIG. 2 that illustrates a position of an archwire in the archwire slot.
Figure 4A:
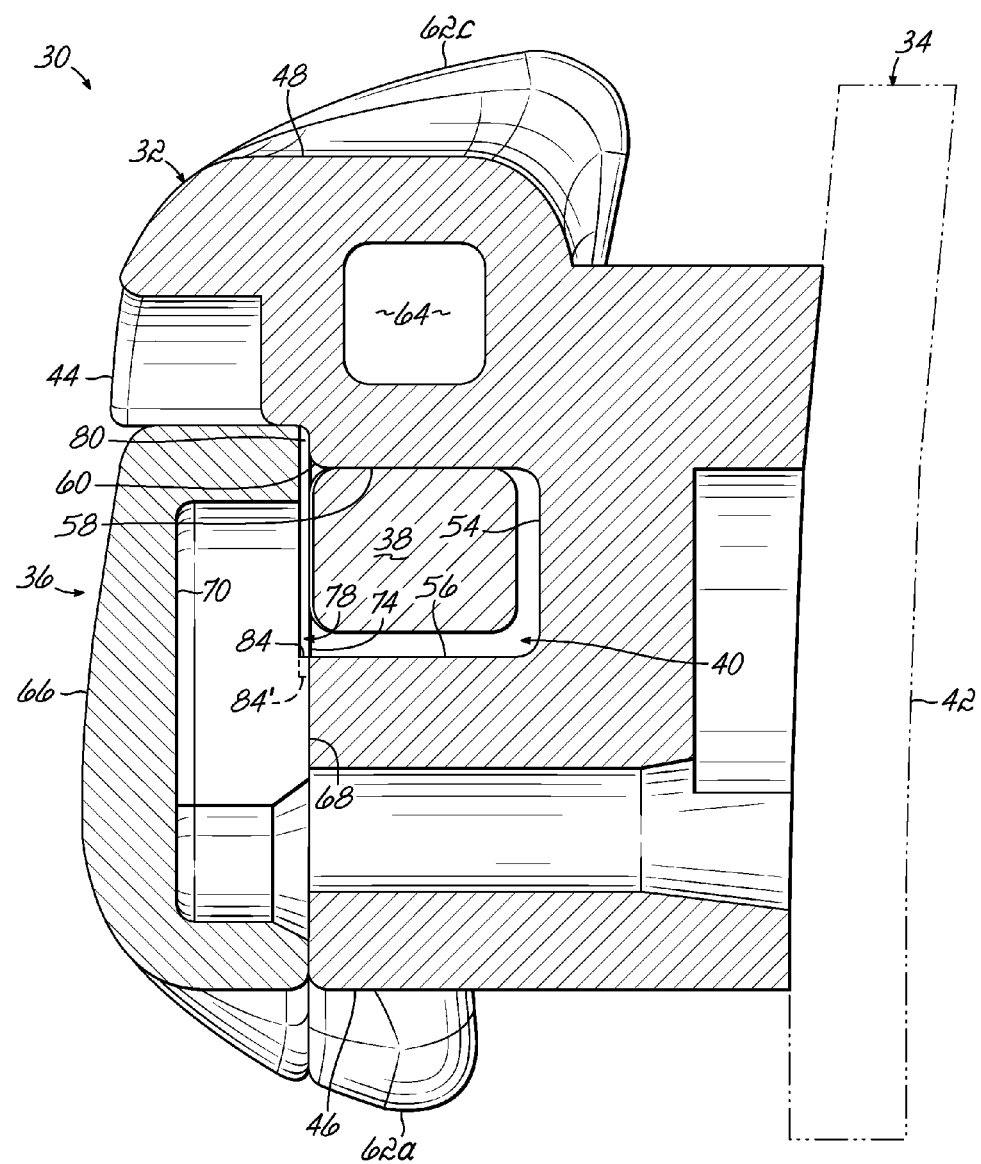
FIG. 4A is a cross-sectional view taken along section line 4A-4A of FIG. 2 that illustrates a position of the archwire in the archwire slot.

Accordingly, as shown in FIG. 4A, when the closure member 36 is in the closed or ligating position, the archwire control structure 72, opposing side walls 56, 58 and base surface 54 of the archwire slot 40 form a four-sided boundary to retain the archwire 38 in the archwire slot 40. As is known, the archwire 38 may have cross-sectional dimensions that are generally less than the corresponding cross-sectional dimensions of the four-sided boundary, as shown. In this way, the archwire 38 is not tightly restrained by the closure member 36 in the archwire slot 40. Due to the relative size difference, the archwire 38 may bend and/or move in the archwire slot 40 relative to the orthodontic bracket 30.

In particular, when the closure member 36 is in the closed position, the projecting portions 74, 76 with recessed area 78 are positioned labially of the archwire slot 40 and form the labial boundary thereof. Thus, movement of the archwire 38 may cause the archwire 38 to contact one or both of projecting portions 74, 76. Since the projecting portions 74, 76 forms the labial boundary, the archwire 38 may not contact another portion of the closure member 36 during treatment.

Further in this regard, and as shown in FIG. 4A, the occlusal side wall 84 of the recessed area 78 may reside in the plane of opposing side wall 56, as shown, or may be positioned occlusally thereof (labeled 84'). Thus, when the archwire 38 contacts the closure member 36, it will not contact any portion of the closure member 36 other than one or both of the projecting portions 74, 76. In other words, the recessed area 78 encompasses the labial boundary between the projecting portions 74, 76.

Accordingly, due to the archwire control structure 72, the rotational forces may be predetermined and controlled to a greater extent because the moment arm formed thereby may be both larger and more consistent throughout orthodontic treatment. By way of example and as illustrated in FIG. 4B, the archwire 38 may be oriented such that it contacts both the bracket body 32 and the projecting portion 74, thereby forming a moment arm 88 defined by the distance between the contact points. As shown, with the archwire 38 in this orientation, a force 90 generated by the archwire 38 may produce a torque 92, due to the moment arm 88, to rotate the bracket 30 (and tooth) into the desired position. By way of comparison with the bracket 14 shown in FIG. 1, the moment arm 88 may be at least as large as the moment arm 24 for equivalent bracket dimensions. In addition, with reference to FIG. 4B, since the contact points between the archwire 38 and the bracket 30 are relatively constant, as the contact points on the closure member 36 (i.e., on the archwire control structure 72) remain consistent during treatment, the moment arm 88 remains relatively consistent compared to the moment arm 24 of FIG. 1, as described above.

With regard to consistency of the contact points, according to embodiments of the invention, the contact points between the bracket body 32 and the closure member 36 may not substantially shift as treatment progresses. Accordingly, the moment arm and thus the torque applied to the tooth are more consistent. Thus, the rotational forces are more predictable. By way of example, with reference to FIGS. 2 and 4B, the archwire 38 may be oriented in a non-parallel manner relative to the archwire slot 40. During treatment, where the archwire 38 bends, due to movement of the bracket 30, such that an apex (not shown) of the bend forms between the projecting portions 74, 76, and within the recessed area 78, the apex does not contact another location. That is, the archwire 38 does not contact the surface 86. Therefore, no forces develop between the surface 86 and the archwire 38 that would lead to an unpredictable moment arm. Rather, the archwire 38 remains in contact with one of the projecting portions 74, 76 and the moment arm 88 may remain substantially constant until the bracket 30 moves to an orientation where the archwire 38 does not contact the closure member 36. At this point, the archwire 38 may be substantially aligned with the archwire slot 40. While the embodiment shown illustrates the archwire 38 contacting the projecting portion 74 and the archwire slot 40 on the base surface 54 at the distal end 52 thereof, it will be appreciated that the orientation of the archwire 38 may be reversed. For example, the archwire 38 may have an orientation whereby contact occurs at the projecting portion 76 and at the mesial end 50 of the base surface 54. Such a configuration will provide the benefits and advantages as described above related to a more consistent moment arm and torque, but provide rotation in a direction opposite to that described above.

Figure 5:
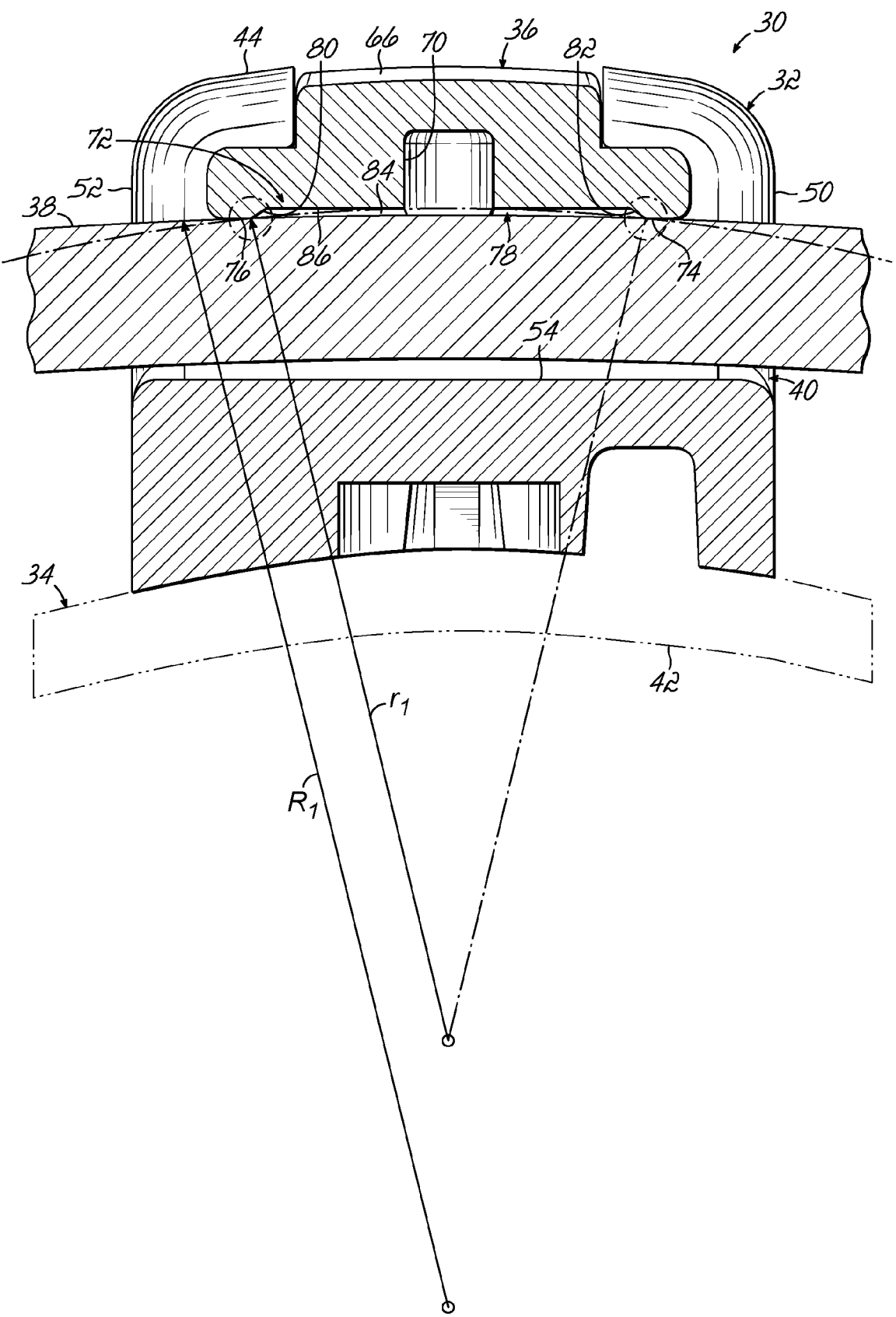
FIG. 5 is a cross-sectional view similar to FIG. 4B that illustrates a finishing position of the archwire in accordance with the embodiment shown in FIG. 2.

In the finished state, as shown in FIG. 5, the archwire 38 may make two points of contact on the archwire control structure 72. By way of example, the archwire 38 makes contact with each of the projecting portions 74, 76. Near the end of treatment, this configuration mimics the fine rotation control provided by traditional methods of ligation, such as ligating an archwire to a bracket with traditional ligatures, and thereby improves finishing in clinical cases. It will be appreciated that for the anterior section of lower and upper jaws, the flat occlusal edges of the incisor teeth magnify distortions in rotation such that fine control is desired and fine control may be provided according to embodiments of the present invention.

Given that the archwire-closure member contact points are limited to specific, predetermined locations in the embodiments shown, e.g., the projecting portions 74, 76, the clinician may be more likely to be able to assess the clinical result of a change in treatment for a given orthodontic bracket, archwire, and tooth orientation or may be able to affect a certain rotational motion more quickly. Furthermore, the moment arm formed by contact between the archwire and the archwire control structure may be maximized to rotate the bracket 30 and tooth in more efficient and optimal manner.

Various modifications may be made to the archwire control structure 72 in accordance with the description set forth above. For example, the desired contact locations between the archwire 38 and the closure member 36 may be adjusted to allow for a particular torque or to allow use of archwires of differing dimension. In this regard, the depth of the recessed area 78 may be changed to accommodate changes in the bracket and/or archwire dimensions. In one embodiment, the recessed area 78 has minimum depth such that the apex or deepest central point thereof together with the projecting portions 74, 76 on the mesial and distal ends thereof form or define a radius of curvature, r1, that is less than the radius of curvature, R1, of the archwire 38. Further in this regard, to change the radius of curvature, r1, it will be appreciated that while the surface 86 is depicted as a near-planar surface having side walls 80, 82, 84, embodiments in accordance with aspects of the invention are not so limited. By way of example, the surface 86 may be a generally non-planar surface, such as a uniform arc (labeled 86' in FIG. 4B) that extends from the mesial to the distal sides of the closure member 36 with or without side walls 80, 82, 84. The radius of curvature, r1, may then be defined by the configuration of the arc. By way of additional example, the radius of curvature, r1, may also be defined by other regular and/or irregular-shaped recessed areas. It will be appreciated that, regardless of the shape of the recess, the concepts employed and features described remain similar.

Additionally, to change the magnitude of the moment arm 88, the recessed area 78 may be extended to cover a larger portion of the lingual surface 68 of the closure member 36. It will be appreciated that moving the projecting portions 74, 76 apart in the mesial-distal direction may further improve the length of the moment arm 88. Maximizing the distance between the two points of contact (e.g., one on the base surface 54 of the archwire slot 40 and the other on the lingual surface 68 of the closure member 36), maximizes the moment arm 88 and, consequently, maximizes the torque for a given force. Accordingly, smaller forces may be used to provide the same amount of torque. In one embodiment, the recessed area 78 extends a sufficient dimension along the lingual surface 68 such that projecting portion 74, 76 reside on the mesial-most and distal-most edges of the closure member 36. In this case, the projecting portions 74, 76 may each appear to be pointed edges oriented toward the archwire slot 40.

Figure 6:
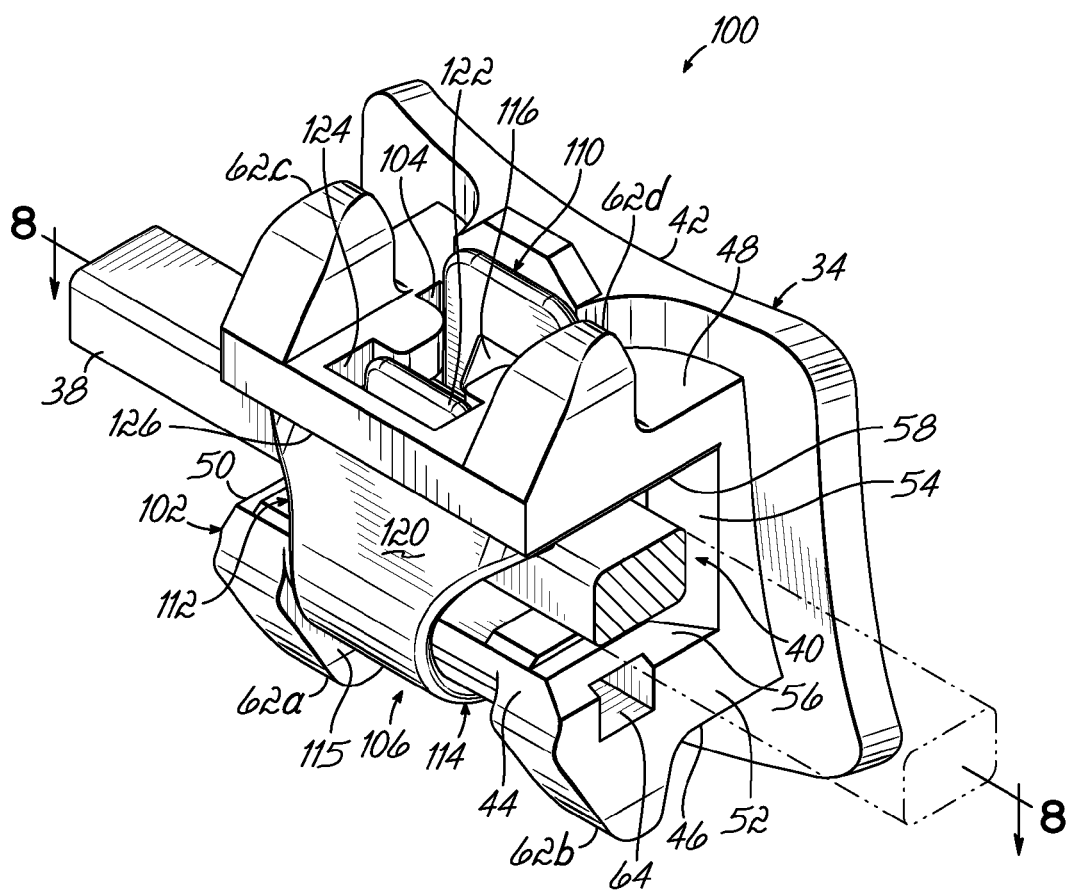
FIG. 6 is a perspective view of an orthodontic bracket holding an archwire in accordance with another embodiment of the invention.

In another embodiment in accordance with aspects of the invention and with reference to FIGS. 6-9, in which like reference numerals refer to like features, an orthodontic bracket 100 similar to those illustrated in FIGS. 2-5 is depicted. With reference specifically to FIG. 6, the orthodontic bracket 100 has a bracket body 102 having an occlusal-gingival slot 104 positioned lingually of the archwire slot 40 and a ligating member, closure member, or a U-shaped clip 106 for sliding movement in the occlusal-gingival direction within slot 104 for retaining/releasing the archwire 38 form the archwire slot 40.

Referring to FIGS. 6 and 7, the clip 106 captivates the archwire 38 within the archwire slot 40 when it is in a closed position. The clip 106 moves within the occlusal-gingival slot 104 from an open position to allow the archwire 38 to be removed from the archwire slot 40 to a closed position (as shown in FIG. 6). The clip 106 includes archwire control structure 108 (described in more detail below) that provides predictable, consistent contact between the archwire 38 and the orthodontic bracket 100 similar to that described above.

With reference to FIG. 7, the clip 106 may be generally U-shaped and may be made from a resilient, flat spring material, such as a cobalt-chrome (Co—Cr) alloy, nickel-titanium (Ni—Ti) alloy, other shape memory alloys, or another suitable material. The clip 106 may be formed from a single sheet of the material and thus the through-thickness of the clip 106 may be uniform. However, it will be appreciated that the clip 106 need not be uniform in thickness depending on, for example, the bracket design and the material from which the clip 106 is made, among other factors.

In one embodiment, the clip 106 has a lingual leg 110 and a labial leg 112 that are connected by a generally lateral section 114. The lingual leg 110 may be of a generally uniform thickness that fits within the occlusal-gingival slot 104 (as shown in FIG. 6). The lingual leg 110 may include a tab 116 that projects from the labial surface thereof generally toward the lateral section 114 or otherwise provides a discontinuity in the overall thickness of the lingual leg 110. Where the lingual leg 110 extends through the occlusal-gingival slot 104, the clip 106 resists unintentional removal because tab 116 may abut a portion of the gingival side 48 of the orthodontic bracket 100 once the clip 106 is moved to the open position. Alternatively, the tab 116 may abut the surface 56 of the archwire slot 40 when in the open position and thereby resist removal of the clip 106 from the bracket body 32.

The lateral section 114 may form a generally smooth arc, as shown, and may cooperate with a portion the occlusal side 46 and/or labial side 44 of the bracket body 102 and may, for example, reside in a channel 115 between the two occlusal tie wings 62a, 62b. The channel 115, in cooperation with other portions of the bracket 100, such as the slot 104, may stabilize mesial-distal movement of the clip 106 when contacted by the archwire 38. The resilient properties of the clip 106, particularly of the lateral section 114, together with the configuration of the lateral section 114 may provide spring-like clamping forces on the bracket body 102 along the occlusal and labial surfaces thereof to resist unintentional movement of the clip 106 in such a way as to expose the archwire slot 40.

Figure 7A:
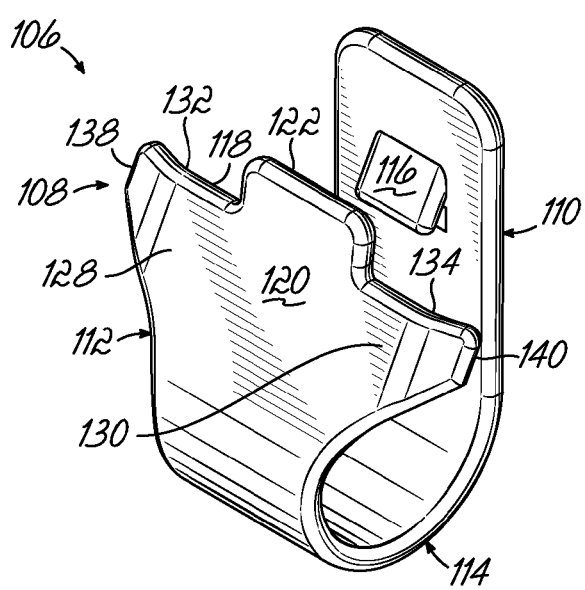
FIG. 7A is a perspective view of a closure member in the illustrative form of a U-shaped clip, as used in the bracket shown in FIG. 6.
Figure 7B:
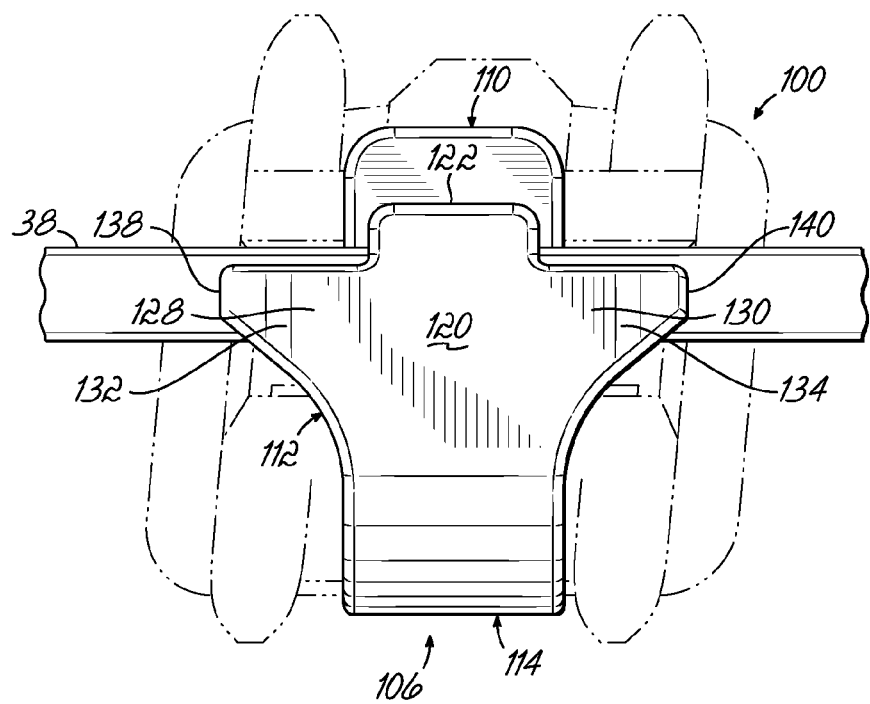
FIG. 7B is a plan view of the bracket of FIG. 6 that illustrates one location of the U-shaped clip relative to the archwire and bracket body, which is shown in phantom line.

With reference to FIGS. 7A and 7B, the labial leg 112 is oriented in a direction generally in the gingival direction at an angle to the lingual leg 110. The labial leg 112 has a lingual surface 118 that projects labially over the archwire slot 40 when the clip 106 is in the closed position and a labial surface 120. In addition, the labial leg 112 may widen relative to the lingual leg 110 and/or lateral section 114, as shown, and may extend the mesial-distal dimension of the archwire slot 40, though the width of the labial leg 112 may be less or more than the length of the archwire slot 40.

Figure 8:
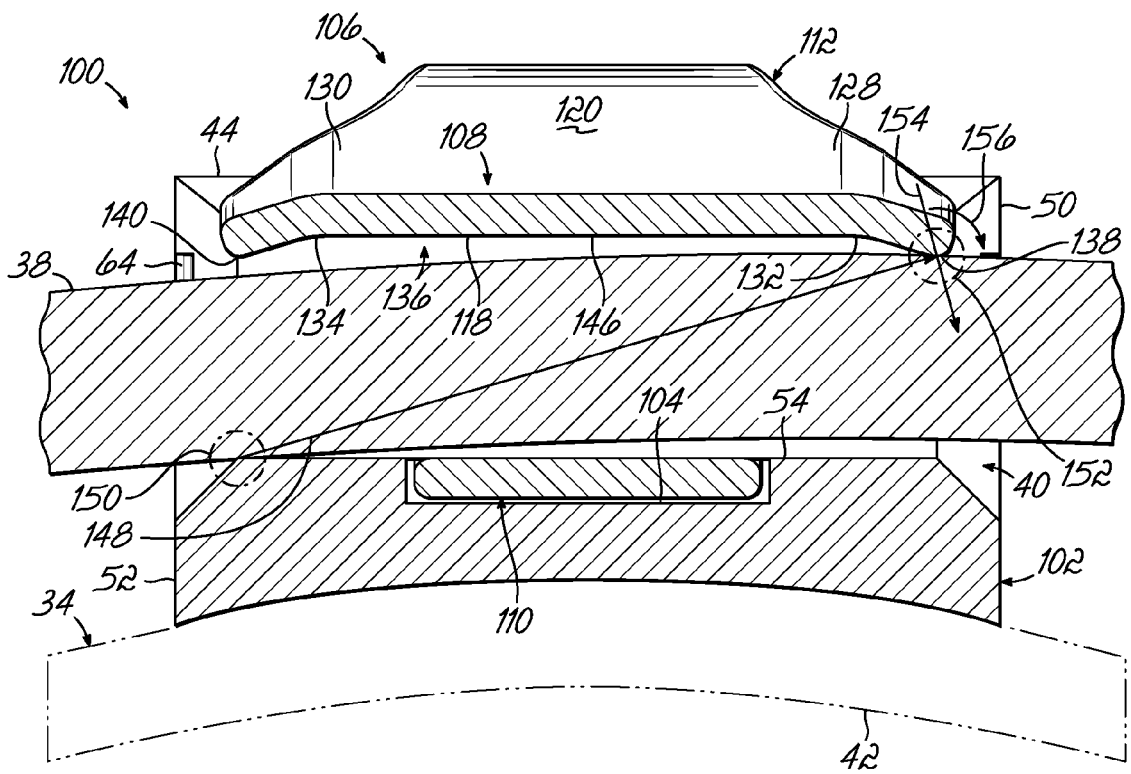
FIG. 8 is a cross-sectional view taken along section line 8-8 of FIG. 6 that illustrates a position of an archwire in the archwire slot.

In one embodiment and with reference to FIGS. 7A and 8, the labial leg 112 includes archwire control structure 108 that may include mesial and distal projections or wings 128, 130 that extend mesially and distally, respectively, from the labial leg 112. In addition, each of the mesial wing 128 and the distal wing 130 has a tip 132, 134 that may extend generally lingually therefrom to form a mesial projecting portion 138 and a distal projecting portion 140, respectively.

As shown in FIG. 8, the tips 132, 134 may be oriented toward the lingual leg 110 such the labial leg 112 may be generally curved in the form of an arc that is convex in the labial direction. By way of example, the labial leg 112 may be curved in the mesial-distal direction over the archwire slot 40, the curve or arc may extend from the mesial projecting portion 138 to the distal projecting portion 140. In one embodiment, the curved form of the clip 106 may be made by bending a flat spring metal such that the clip 106 has a permanent curvature in the mesial-distal direction in the labial leg 112 thereof.

With continued reference to FIG. 8, the curvature defined by the orientation of the mesial and distal wings 128, 130 and tips 132, 134 forms a recessed area 136 with projecting portions 138, 140 being spaced apart in the mesial-distal direction over the archwire slot 40. The recessed area 136 may be defined by a recessed surface 146 that is formed by curvature of the lingual surface 118 of the labial leg 112. As with projecting portions 74, 76 of the embodiment shown in FIGS. 2-5, the projecting portions 138, 140 with recessed area 136 are positioned labially of the archwire slot 40 and form the labial boundary thereof to restrain or limit movement of the archwire 38 beyond a certain amount in the labial direction. In other words, the archwire 38 may move mesially or distally but only a limited direction in any of the gingival, occlusal, lingual, or labial directions, with the projecting portions 138, 140 limiting the movement in the labial direction. However, the recessed area 136 may include a through-hole, cutout, or opening that extends through the clip, as shown in the exemplary embodiment of FIG. 11, for example.

Since the archwire control structure 108 forms the labial boundary, the archwire 38 may not contact any other portion of the clip 106 during orthodontic treatment. In other words, and in the embodiment shown, the archwire 38 may contact only one or both of the projecting portions 138, 140 of the clip 106.

Figure 9:
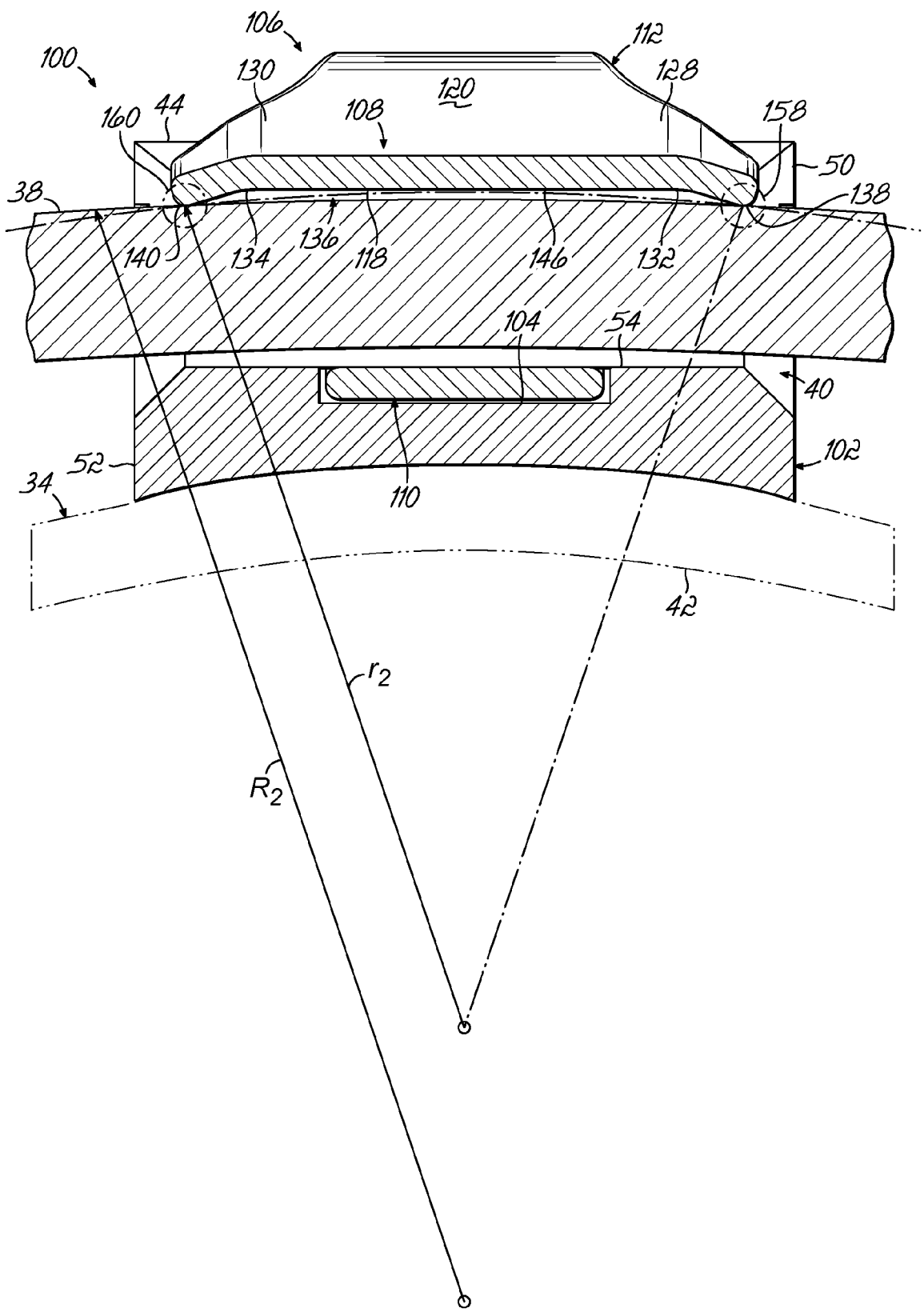
FIG. 9 is a cross-sectional view similar to FIG. 8 that illustrates a finishing position of the archwire in accordance with the embodiment shown in FIG. 6.

The archwire control structure 108, similar to the archwire control structure 72, described above, may provide more consistent contact points between the archwire 38 and the bracket 100 during orthodontic treatment. With reference to FIGS. 8 and 9, the archwire 38 may be oriented in a non-parallel manner relative to the archwire slot 40. By way of example, the archwire 38 may be oriented such that it contacts both the bracket body 102 and the clip 106 thereby forming the moment arm 148, which is defined by the distance between the two contact points. For example, the archwire 38 may contact the distal end 52 of the bracket body 102 at 150 and the projecting portion 138 at 152. As illustrated in FIG. 8, a force 154 having moment arm 148 produces a torque 156 to rotate the bracket 100 (and tooth) into the desired position. By way of comparison with the bracket 14 shown in FIG. 1, the moment arm 148 may be at least as large as the moment arm 24 for equivalent bracket dimensions. In any event, in one embodiment and with reference to FIG. 8, since the contact points between the archwire 38 and the bracket 100 are relatively constant, the moment arm 148 remains relatively consistent compared to the moment arm 24 of FIG. 1.

Furthermore, according to embodiments of the invention, the two-point contact configuration shown in FIG. 8 between archwire 38 and both of the bracket body 102 and the clip 106 may not substantially shift as treatment progresses. Therefore, no forces may develop other than at one or both of the projecting portions 138, 140. While the embodiment shown illustrates the archwire 38 contacting the projecting portion 138 and the archwire slot 40 on the base surface 54 at the distal end 52 thereof, it will be appreciated that the orientation of the archwire 38 may be reversed. For example, the archwire 38 may have an orientation whereby contact occurs at the projecting portion 140 and the mesial end 50 of the base surface 54. Therefore, the moment arm 148 may remain substantially constant until the bracket body 102 moves to an orientation where the archwire 38 does not contact the clip 106. In this situation, the archwire 38 may be substantially aligned with the archwire slot 40.

As shown in FIG. 9, the archwire 38 may make two points or locations of contact with the bracket 100, for example, two-point contact may include contact at 158 and 160 between the archwire 38 and the archwire control structure 108. In particular, the archwire 38 makes contact with each of the projecting portions 138, 140. To provide the desired contact locations between the archwire 38 and the clip 106, for example, at both projecting portions 138, 140, the shape of the recessed area 136 may be changed to accommodate changes in the bracket and/or archwire dimensions. In one embodiment, as shown in FIG. 9, the recessed area 136 has minimum curvature such that the apex thereof or deepest central point in combination with the projecting portions 138, 140 form or define a radius of curvature, $r_2$, that is less than the radius of curvature, $R_2$, of the archwire 38. In this regard, the radius of curvature, $r_2$, may decrease by increasing the depth of the recessed area 136. Other configurations of the recessed area 136 may produce similar results, for example, the recessed area 136 may be defined by other regular and irregular-shaped recessed areas that define a radius of curvature that is less than the radius of curvature, $R_2$, of the archwire 38.

Various additional or alternative modifications may be made to the archwire control structure 108 in accordance with the description set forth above. For example, the dimensions of the clip 106, particularly the distance between the projecting portions 138, 140 may affect the length of the moment arm 148. Maximizing the distance between the two points of contact, maximizes the moment arm 148 and, consequently, maximizes the torque available to rotate the tooth. The length of the moment arm 148 may be increased by increasing the width of the labial leg 112, and particularly increasing the distance between the projecting portions 138, 140; by increasing the overall width of the labial leg 112; by increasing the size of the wings 128, 130; or by changing the orientation between the wings 128, 130 and tips 132, 134. In one embodiment, the projecting portions 138, 140 approach or are proximate the respective mesial distal sides of the archwire slot 40.

Additionally, the recessed area 136 may form a rectangular shape such that the tips 132, 134 are nearly perpendicular to the archwire slot 40. In addition, the recessed area 136 is sufficiently deep for a given archwire and archwire slot dimension such that the apex of the archwire 38 may not reach the surface 146 or contact another portion of the clip 106 during orthodontic treatment. However, even where the apex in the archwire 38 may shift, possibly due to movement of the teeth, the two-point contact between the archwire and the clip 106 shown in FIG. 8 may not change.

The labial leg 112 may further include an extension 122 that extends generally in the same direction as the lingual leg 110. The extension 122 fits within a retention slot formed 124 by a labial stop 126 (shown in FIG. 6) that extends between tie wings 62c, 62d. The extension 122 may be narrower, the same width, or wider than the lingual leg 110 or labial leg 112 or the lateral section 114. When the clip 106 is in the closed position, the extension 122 may also stabilize the clip 106 against mesial-distal movement when in contact with the archwire 38. Furthermore, the extension 122 may contact the labial stop 126 to substantially prevent the clip 106 from unintentionally releasing the archwire 38. In this way, the extension 122 may further stabilize the contact locations between the archwire control structure 108 and the archwire 38 when the archwire 38 is in a non-parallel orientation with respect to the archwire slot 40. Labial movement of the archwire 38 may be further limited by the extension 122 such that the contact points between the archwire 38 and projecting portions 138, 140 are more consistent because the clip 106 may not significantly flex or distort. While FIGS. 6 and 7 depict the clip 106 as including extension 122, it will be appreciated that clip 106 need not have extension 122 and be designed to not substantially flex or distort under the loads that may be experienced during use of the clip 106.

Figure 10:
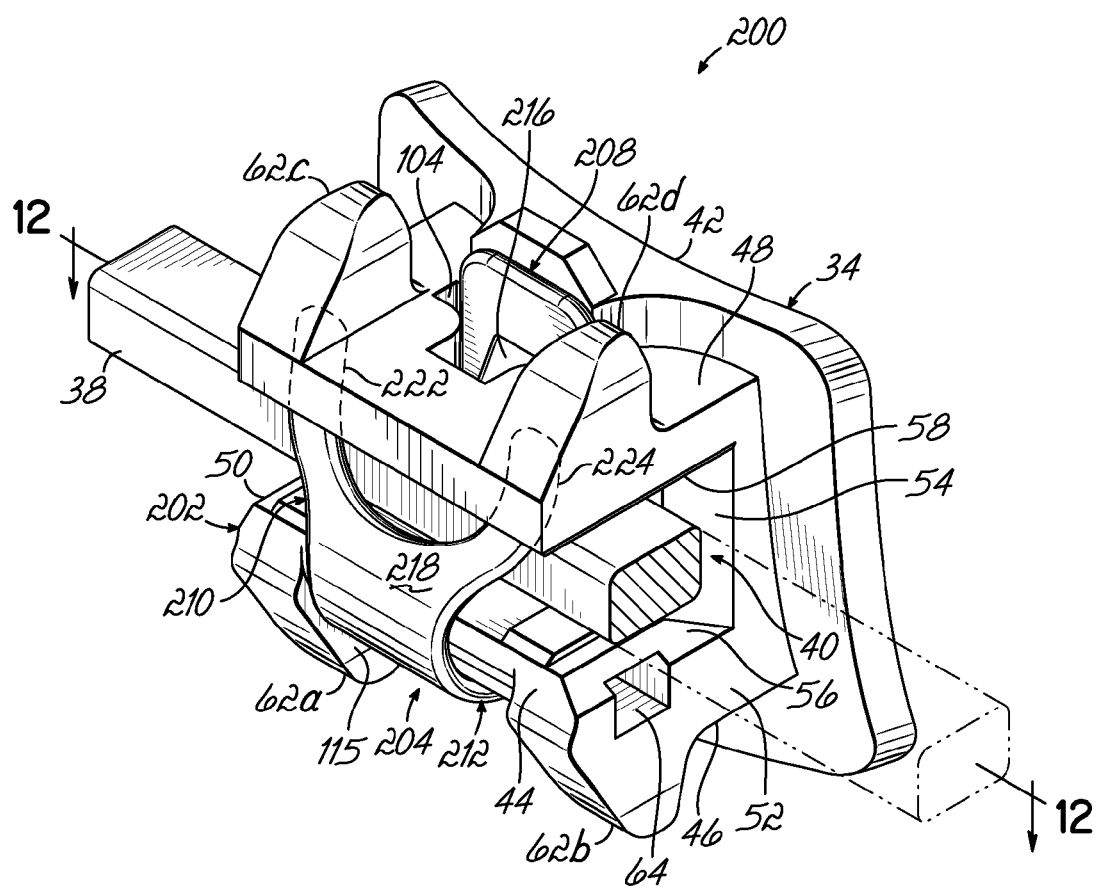
FIG. 10 is a perspective view of an orthodontic bracket holding an archwire in accordance with another embodiment of the invention.

In another embodiment of the invention shown in FIGS. 10-14, in which like reference numerals refer to like features of FIGS. 6-9, the orthodontic bracket 200 is similar to the bracket 100 illustrated in FIGS. 6-9. With reference specifically to FIG. 10, the orthodontic bracket 200 includes a bracket body 202 and a ligating or closure member which in this illustration is a U-shaped clip 204 for sliding movement in the occlusal-gingival direction within slot 104.

The clip 204 is similar in some respects to clip 106 depicted in FIG. 7. Accordingly, as shown in FIG. 10, the clip 204 captivates the archwire 38 within the archwire slot 40 when it is in a closed position. The clip 204 moves within the occlusal-gingival slot 104 to an open position to allow the archwire 38 to be removed from the archwire slot 40.

The clip 204 includes archwire control structure 206 (described in more detail below) that provides more predictable, consistent contact between the archwire 38 and the orthodontic bracket 200. In this regard, the archwire control structure 206 limits contact between the archwire 38 and the clip 204 to specific locations. Further, the specific locations may be predetermined and may not substantially shift during orthodontic treatment. By way of example, the archwire control structure 206 may provide two-point contact between the orthodontic bracket 200 and the archwire 38. In this case, the archwire 38 may contact both the bracket body 202 at one location and the clip 204 at one location. Specifically, the contact points may include a contact point on the archwire control structure 206 and one at the mesial end 50 or distal end 52 of the base surface 54 of the archwire slot 40. In one embodiment, the archwire control structure 206 limits contact between the archwire 38 and the clip 204 to one or two predetermined locations. Two-point contact may also include contact between the archwire 38 and two locations on the archwire control structure 206. That is, the archwire 38 does not contact the bracket body 202. In addition, three- and four-point contact between the archwire 38 and the orthodontic bracket 200 is also contemplated according to embodiments of the present invention.

Figure 11:
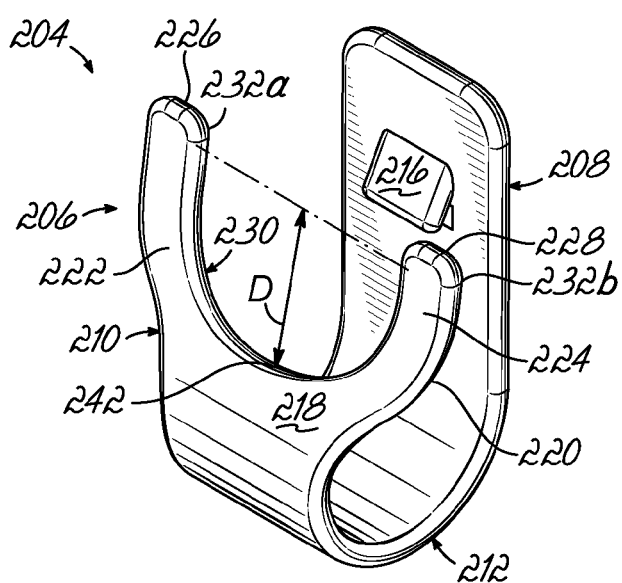
FIG. 11 is a perspective view of a closure member in the illustrative form of a second U-shaped clip, as used in the bracket shown in FIG. 10.

With reference to FIG. 11, the clip 204 may be generally U-shaped and may be made from a single sheet of a resilient, spring material, such as a suitable metal. The metal may be cobalt-chrome (Co—Cr) alloy, nickel-titanium (Ni—Ti) alloy, other shape memory alloys, or other suitable material. Thus, the through-thickness of the clip 204 may be uniform. The clip 204 may be formed by bending the flat spring metal to have the U-shape. However, it will be appreciated that the clip 204 need not be uniform in thickness depending on, for example, the bracket design and the material from which the clip 204 is made, among other factors. In one embodiment, the clip 204 is made from a flat spring metal.

In the exemplary embodiment shown in FIG. 11, the clip 204 has a lingual leg 208 and a labial leg 210 that are connected by a lateral section 212. The lingual leg 208 is generally uniform in thickness and fits within the occlusal-gingival slot 104. The lingual leg 208 may include a tab 216 that functions similar to tab 116 shown in FIG. 7.

The lateral section 212 may form a generally smooth arc, as shown, and may cooperate with a portion the occlusal side 46 and/or labial side 44 of the bracket body 202. In one embodiment, the resilient properties of the clip 204 together with the configuration of the lateral section 212 may provide spring-like clamping forces that improve friction between the clip 204 and the bracket body 202 along a portion of the occlusal and labial surfaces thereof to resist unintentional movement of the clip 204 in such a way as to expose the archwire slot 40.

In one embodiment, the clip 204 may be formed such that the labial leg 210 projects gingivally from the lateral section 212 to form a U-shaped cross section. In this configuration, the labial surface 218 forms a portion of the labial side 44 of the bracket 200, though embodiments of the present invention are not so limited, as a portion of the labial leg 210 and/or the lateral section 212 may extend through a slot or other recess formed in the bracket body 202 on the occlusal side 46 thereof. Furthermore, the lingual surface 220 of the labial leg 210 projects labially over the archwire slot 40 when the clip 204 is in the closed position, as shown in FIG. 13, and forms the labial boundary thereof.

In the exemplary embodiment illustrated in FIGS. 10-14, the labial leg 210 includes a mesial portion 222 and a distal portion 224. Rather than a recessed area between the mesial portion 222 and distal portion 224, the mesial and distal portions 222, 224 may define a generally U-shaped cutout 230 such that labial leg 210 appears bifurcated, i.e., the clip 204 may be a so-called bifurcated clip. The cutout may have a depth D from the end of the mesial and distal portions 222, 224 to the apex of the cutout 230 that is greater than the occlusal-gingival dimension of the archwire slot 40. It will be appreciated, however, that the mesial and distal portions 222, 224 may define other configurations, such as a rectangular notch, having a similar depth D.

Figure 13:
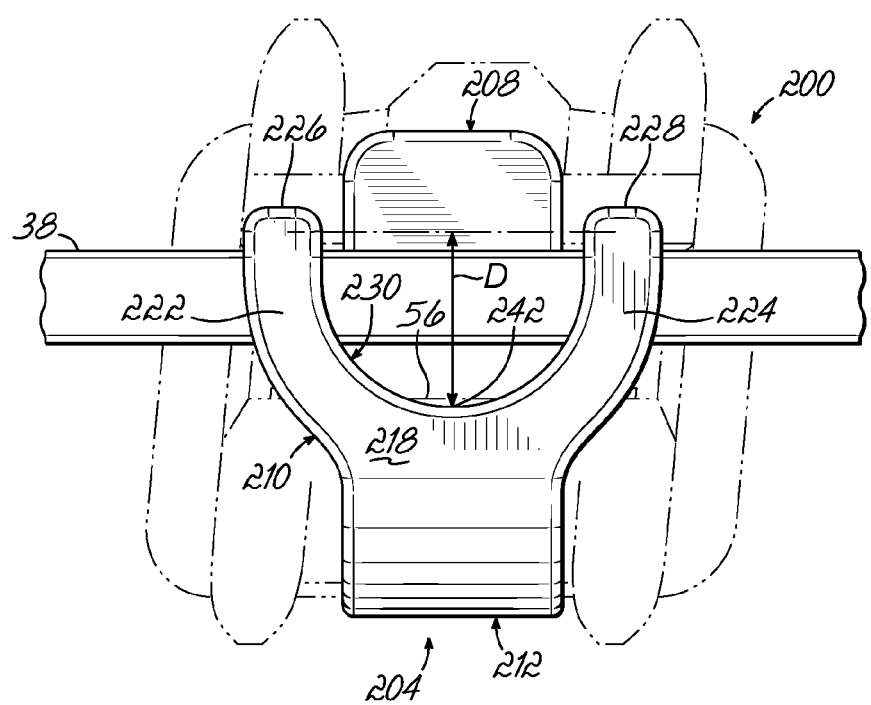
FIG. 13 is a plan view of the bracket of FIG. 10 that illustrates one location of the U-shaped clip relative to the archwire and bracket body, which is shown in phantom line.

In addition, as shown best in FIGS. 11 and 13, the labial leg 210 may widen relative to the lingual leg 208 and lateral section 212. In this regard, the mesial portion 222 and distal portion 224 of the labial leg 210 may be spaced apart in the mesial-distal direction along the archwire slot 40. Specifically, the mesial-distal dimension from the mesial edge of mesial portion 222 to the distal edge of distal portion 224 may be greater than the width of the lateral section 212 and/or the lingual leg 208. However, the maximum mesial-distal dimension of the labial leg 210 may be less or more than the dimension of the archwire slot 40. In one embodiment, the maximum width of the labial leg 210 may extend the full width of the mesial-distal dimension of the archwire slot 40 or be proximate thereto.

Figure 12:
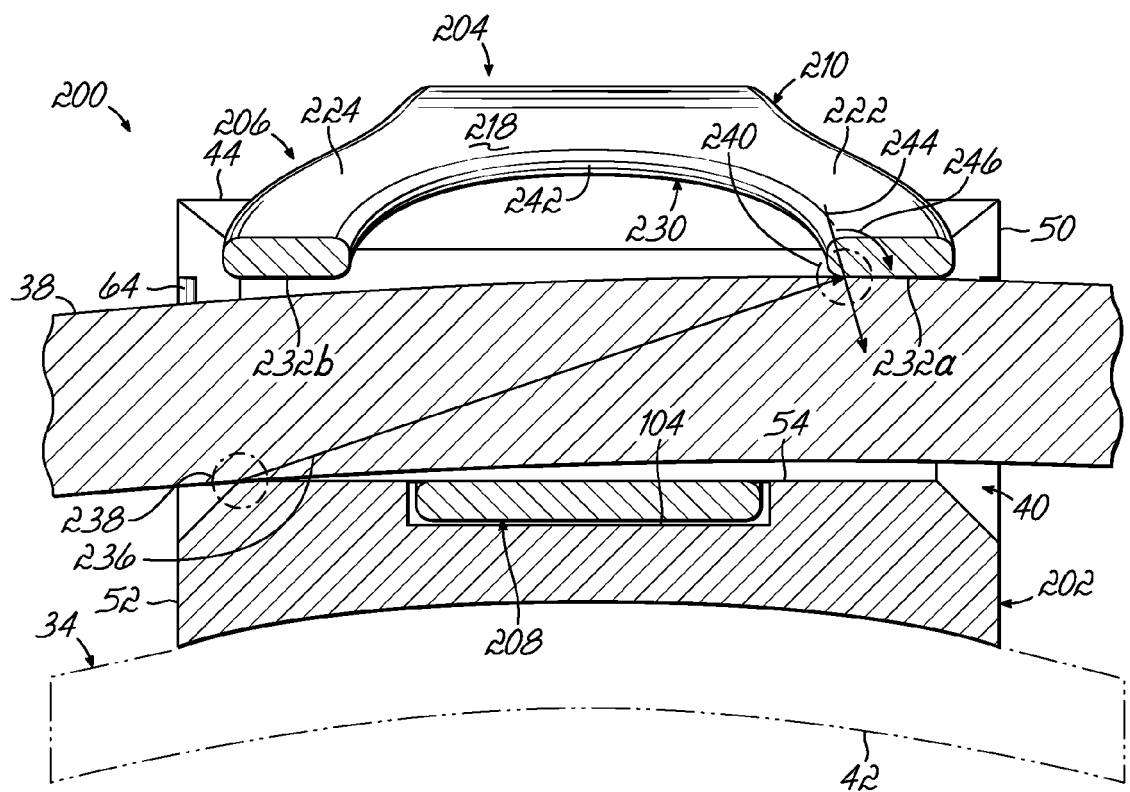
FIG. 12 is a cross-sectional view taken along section line 12-12 of FIG. 10 that illustrates a position of an archwire in the archwire slot.

As shown in FIGS. 11, 12, and 13, in one embodiment, the labial leg 210 includes archwire control structure 206. The archwire control structure 206 may include mesial and distal lingual surfaces 232a, 232b of mesial portion 222 and distal portion 224, respectively. As with projecting portions 74, 76 and projecting portions 138, 140, described above, the mesial and distal lingual surfaces 232a, 232b are positioned labially of the archwire slot 40 when the clip 204 is in the closed position. The surfaces 232a and 232b form the labial boundary of the archwire slot 40 to restrain or limit movement of the archwire 38 beyond a certain amount in the labial direction. In one embodiment, the archwire 38 may not contact another portion of the clip 204 during orthodontic treatment. In other words, and in the embodiment shown, the archwire control structure 206 limits contact between the archwire 38 and clip 204 to one or both of the mesial and distal lingual surfaces 232a, 232b. Since the contact points are limited to two specific, predetermined locations, e.g., the mesial and distal lingual surfaces 232a, 232b, the clinician may be more likely to be able to assess the clinical result of a change in treatment for a given orthodontic bracket, archwire, and tooth orientation. Furthermore, as set forth in more detail below, a moment arm is formed by contact between the archwire 38 and the archwire control structure 206 and the archwire 38 and the bracket body 202 is more consistent over the course of treatment.

By way of example and with reference to FIG. 12, the archwire 38 may be oriented in a non-parallel manner relative to the archwire slot 40 such that it contacts both the bracket body 202 and the archwire control structure 206 of the clip 204. This orientation forms a moment arm 236 defined by the distance between the two contact points. Specifically, the archwire 38 may contact the bracket body 202 at the base surface 54 at location 238 of the archwire slot 40 and the mesial lingual surface 232a at location 240 of the archwire control structure 206 to form moment arm 236. Where the archwire 38 exerts a force 244 having moment arm 236, a torque 246 is created to rotate the bracket 200 and tooth.

Furthermore, according to embodiments of the invention, the two-point contact configuration shown in FIGS. 12 and 13 between the bracket body 202 and the clip 204 may not shift as orthodontic treatment progresses even though the archwire may move or bend within the archwire slot 40. For example, during treatment, where the archwire 38 bends such that an apex (not shown) of the bend forms between the mesial portion 222 and distal portion 224 of the labial leg 210, i.e., in the cutout 230, the archwire 38 does not contact the clip 204 other than at one or both of the mesial and distal lingual surfaces 232a, 232b. Because the archwire control structure 206 limits contact to two locations on the clip 204, the moment arm 236 may not change significantly during treatment. Thus, adjustments to the force 244, for example, by changing the archwire 38, may produce more predictable rotational movement of the bracket 200. While the embodiment shown illustrates the archwire 38 contacting the mesial lingual surface 232a and the archwire slot 40 on the base surface 54 at the distal end 52 thereof, it will be appreciated that the orientation of the archwire 38 may be reversed. For example, the archwire 38 may have an orientation whereby contact occurs at the distal lingual surface 232b and the mesial end 50 of the base surface 54.

In view of the above and with reference to FIG. 13, various configurations of the archwire control structure 206 may be used to control the contact points. For example, the depth D of the cutout 230 may be sufficient to prevent contact between the archwire 38 and surfaces other than the surfaces 232a and 232b. That is, the cutout 230 may be sufficient to allow a bend or apex of the archwire 38 to pass between the mesial and distal portions 222, 224 should a bend develop during treatment. In particular, in one embodiment, the depth D of the cutout 230 is sufficient to position the apex 242 of the cutout 230 in the plane of opposing side wall 56, or gingivally thereof, as shown, for a given archwire and archwire slot dimensions. However, the depth D may depend on the shape of the lateral section 212 and the labial leg 210. In any case, even where the apex in the archwire 38 may shift, possibly due to movement of the teeth or installation of the archwire 38, the two-point contact between the archwire 38 and the clip 204, as shown in FIGS. 12 and 13, may not significantly change. Therefore, the moment arm 236 may remain substantially constant until the bracket 200 moves to an orientation where the moment arm 236 ceases to exist, i.e., when the tooth reaches the selected position.

Additionally, changes to the moment arm 236 may be selected by changing the configuration of the mesial and distal portions 222, 224. For example, while the mesial and distal portions 222, 224 are shown to have an axis of symmetry about the longitudinal axis of the clip 204 (i.e., a symmetrical bifurcation), the embodiments of the invention are not so limited. Accordingly, the positions of the mesial and distal portions 222, 224 may not be equally spaced relative to the mesial-distal dimension of the archwire slot 40. Similarly, the mesial and distal portions 222, 224 may vary in width relative to one another and change the moment arm 236. By way of additional example, by increasing the width of the labial leg 210 and particularly the distance between the mesial and distal portions 222, 224; by increasing the overall mesial-distal width of the labial leg 210; or by decreasing the individual size of one or both of the mesial and distal portions 222, 224, the length of the moment arm 236 may be increased. In other words, the dimensions of the clip 204, particularly the distance between mesial and distal lingual surfaces 232a, 232b may affect the length of the moment arm 236.

It will be appreciated that maximizing the distance between the two points of contact (e.g., between contact on the base surface 54 of the archwire slot 40 and contact on the archwire control structure 206 of the clip 204), maximizes the moment arm 236 and, consequently, maximizes rotation control. It will be further appreciated that with a consistently larger moment arm, smaller forces may generate an equivalent amount of torque. By way of comparison with the bracket 14 shown in FIG. 1, the moment arm 236 of the embodiment shown in FIG. 10 may be at least as large as the moment arm 24 for equivalent bracket dimensions. In addition, with reference to FIG. 12, since the contact locations, (e.g. at 238 and 240) between the archwire 38 and the bracket 200 are relatively constant, the moment arm 236 remains relatively consistent compared to the moment arm 24 of FIG. 1, as described above.

With reference to FIGS. 10, 11, and 13, in one embodiment, the mesial and distal portions 222, 224 may further include opposing extensions 226, 228, respectively. Opposing extensions 226, 228, extend generally in the same direction as the lingual leg 208 from the mesial and distal portions 222, 224, respectively. The opposing extensions 226, 228 may be configured to contact a portion of the bracket body 202 to substantially prevent the clip 204 from unintentionally releasing the archwire 38 during treatment. For example, the opposing extensions 226, 228 may fit within mesial and distal retention slots (not shown) formed in the opposing side wall 58 of the archwire slot 40 in the bracket body 202. In this regard, the opposing extensions 226, 228 may further stabilize the contact locations between the archwire control structure 206 and the archwire 38 when the archwire 38 is in a non-parallel orientation with respect to the archwire slot 40. Furthermore, opposing extensions 226, 228 may allow the force 244 at contact to be greater and therefore the torque 246 on the bracket 200 to be greater, to rotate the tooth more quickly. As with the extension 122 of the clip 106 of FIG. 7, when the clip 204 is in the closed position, the opposing extensions 226, 228 may also stabilize the clip 204 against mesial-distal movement due to sliding contact with the archwire 38. While FIGS. 10 and 11 depict the clip 204 as including opposing extensions 226, 228, it will be appreciated that clip 204 need not have opposing extensions 226, 228 and be designed to not substantially flex or distort under the loads that may be experienced during use of the clip 204.

Figure 14:
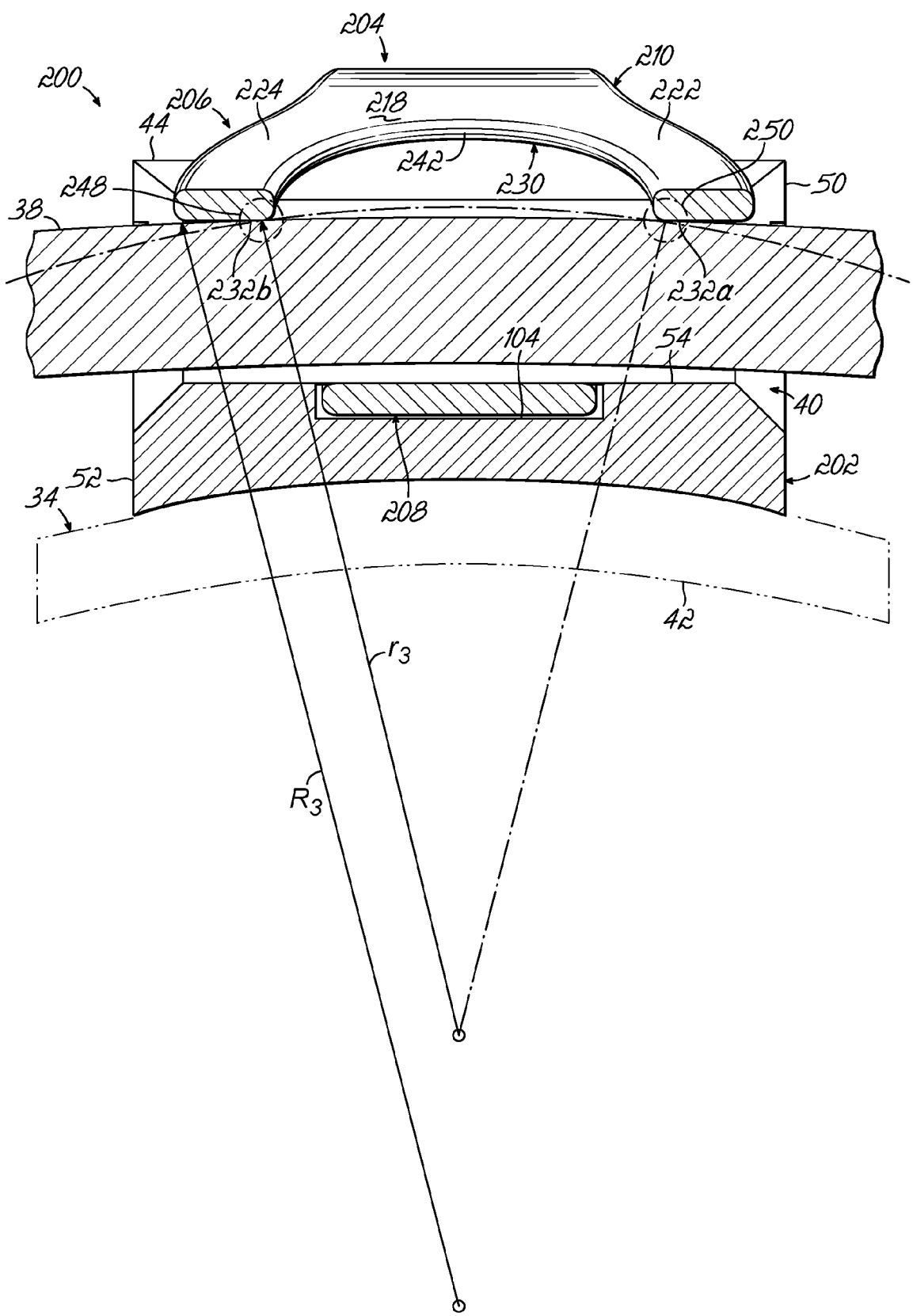
FIG. 14 is a cross-sectional view similar to FIG. 12 that illustrates a finishing position of the archwire in accordance with the embodiment shown in FIG. 10.

As set forth above and shown in FIG. 14, the archwire 38 may make two points of contact on the archwire control structure 206. For example, the archwire 38 may make contact with each of the mesial and distal lingual surfaces 232a, 232b at locations 248 and 250. Similar to the previous embodiments, near the end of treatment this configuration may mimic the fine rotation control provided by traditional methods of ligation and thereby improve finishing in clinical cases.

To that end, to provide the desired contact locations between the archwire 38 and the clip 204, the dimensions of the clip 204 may be changed similar to that described above. For example, the distance between the mesial and distal portions 222, 224 of the labial leg 210, may be changed to accommodate changes in the bracket and/or archwire dimensions. In one embodiment, the distance between the mesial and distal portions 222, 224 allows the archwire 38 to bend to a minimum curvature. However, unlike the embodiments of the invention described above, the radius of curvature, $r_3$, of the clip 204 is not limited by a third location between the mesial and distal portions 222, 224 since the cutout 230 is open. Therefore, where an archwire forms an apex between the mesial and distal portions 222, 224, the apex may pass without any contact with another portion of the clip 204. Thus, the radius of curvature, $r_3$, will be smaller than the radius of curvature $R_3$ of the archwire 38, as shown in FIG. 14.

While the above-described exemplary embodiments include orthodontic brackets that are so-called self-ligating brackets, i.e., the bracket includes a moveable closure member, such as a ligating slide or clip, embodiments of the invention are not limited to brackets that are designed with a moveable closure member coupled thereto. In this regard, and by way of example, embodiments of the present invention include a removable ligating member, such as an elastic or resilient cover that is not meant to be permanently couple to the bracket but is configured to be a separate element selectively coupled to or removed from the bracket.

Figure 15:
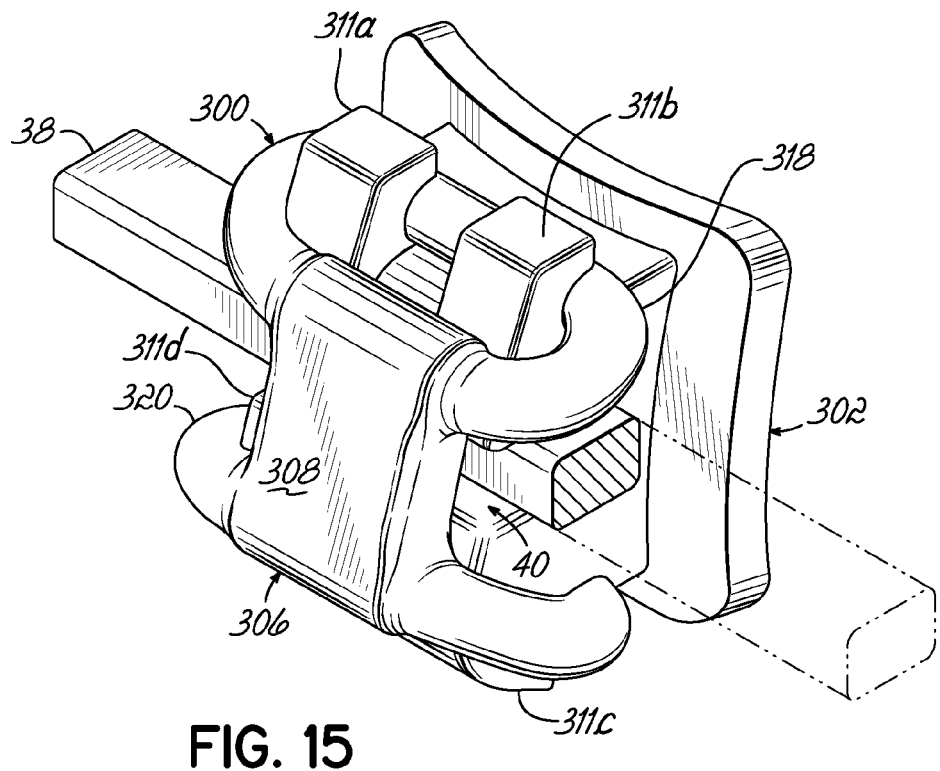
FIG. 15 is a perspective view of a removable ligating member coupled to a bracket for holding an archwire in accordance with another embodiment of the invention.
Figure 16:
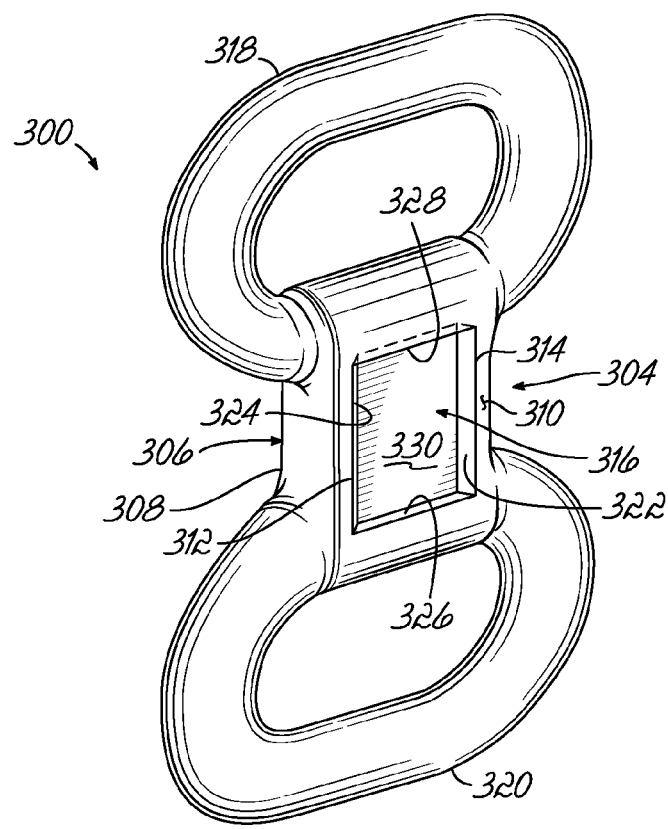
FIG. 16 is a perspective view of the removable ligating member, as used on the bracket shown in FIG. 15.

Accordingly, in another embodiment of the invention shown in FIGS. 15 and 16, in which like reference numerals refer to like features of FIGS. 2-14, an orthodontic member 300, which, in this illustration, is a removable ligating member or cover, may be secured to a conventional edgewise bracket. By way of example, such members are described (albeit in the context of self-ligating brackets) in commonly-owned, co-pending U.S. application Ser. No. 12/622,090, which is incorporated by reference herein in its entirety. Member 300 may be attached to an edgewise bracket 302 having tiewings 311a-d and may be made from an elastomeric material or hard plastic, though the member 300 may be made from other suitable materials.

As shown in FIG. 15, the member 300 is configured to be releasably coupled to the bracket 302 and, when coupled to bracket 302, captures the archwire 38 within archwire slot 40. The member 300 includes archwire control structure 304 that provides predictable, consistent contact between the archwire 38 and the member 300. As with the archwire control structures 72, 108, 206, each described above, the archwire control structure 304 may provide two-point contact between the edgewise bracket 302 and the archwire 38 or two-point contact between the archwire 38 and the member 300.

To this end, in one exemplary embodiment shown in FIGS. 15 and 16, the member 300 includes a main body 306 having labial and lingual surfaces 308, 310. In one embodiment, the lingual surface 310 includes archwire control structure 304 thereon. By way of example, the archwire control structure 304 may include a first projecting portion 312 and second projecting portion 314 separated by a recessed area 316. Projecting portions 312, 314 are configured similarly to projecting portions 74, 76 or projecting portions 138, 140, described above, and have similar functions. Similarly, recessed area 316 is configured similar to the recessed area 78, 136, as well as having similar functions thereof. Accordingly, the recessed area 316 may include a blind recess (as shown) or may include a through-hole or cutout. In one embodiment, the recessed area 316 is defined by a mesial side wall 322, a distal side wall 324, an occlusal side wall 326, and gingival side wall 328 and a recessed surface 330. The recessed surface 330 being similar to surfaces 86, 146 described above.

The member 300 also includes an engaging member, such as engaging members 318, 320 extending from the main body 306, which are configured to releasably couple the member 300 with bracket 302. For example, in one embodiment, the engaging members 318, 320 may include a pair of stretchable closed loops. The engaging members 318, 320 may be stretched over and secured with the tiewings 311a-d. It will be appreciated that the member 300 or a portion thereof may not protrude into the archwire slot 40.

When secured to the bracket 302, a portion of the lingual surface 308 of the main body 306 extends over the archwire slot 40, as shown. Accordingly, the archwire control structure 304 forms the labial boundary of the archwire slot 40. As set forth in the exemplary embodiments above, the archwire 38 may move in the mesial and distal directions. However, the archwire control structure 304 limits movement beyond a certain distance in the labial direction. By way of example, the first and second projecting portions 312, 314 may form the labial boundary of the archwire slot 40. Accordingly, the archwire 38 may contact either or both projecting portions 312, 314 should the archwire 38 be in sufficient non-parallel alignment. By controlling the contact locations, a moment arm formed by contact between the archwire control structure 304 and the archwire 38 and between the base surface 54 and the archwire 38 may be controlled. In order to control the contact locations, in one embodiment, the occlusal side wall 326 resides in the same lingual-labial plane as the occlusal side wall 56 of the archwire slot 40 or occlusally thereof. In another embodiment, the gingival side wall 328 is in the same lingual-labial plane as the gingival side 58 of the archwire slot 40 or gingivally thereof. It will be appreciated that it may be desirable to form a cavity or through hole in the main body 306 rather than the blind recessed area 316.

In another embodiment of the invention, a method of correcting malpositioned teeth includes applying a plurality of orthodontic brackets constructed according to at least one of the embodiment of the invention as shown in FIGS. 2, 6, 10, and 15 to teeth of a patient, and retaining an archwire 38 in the respective archwire slot 40 of the orthodontic bracket with the closure members, for example, closure member 36, clip 106, clip 204, or removable ligating member 300 in the closed positions such that the archwire 38 contacts archwire control structure, such as at least one of the first or second projecting portions 74, 76; at least one of first or second projecting portions 138, 140; at least one of first or second lingual surfaces 232a, 232b; or at least one of projecting portions 312, 314 and without contacting another portion of the closure member 36, clip 106, clip 204, or member 300. For example, the archwire 38 may not contact the recessed area 78, recessed area 136, or recessed area 316.

In one embodiment, the recessed area 78, 136, or 316 and the first and second projecting portions 74, 76 or 138, 140 or 312, 314 of closure member 36, clip 106, or member 300, respectively, define respective curved surfaces, and the respective curves of the curved surfaces each have a radius of curvature that is less than a radius of curvature of the portion of the archwire 38 retained in the respective bracket.

In another embodiment, the method includes retaining the archwire 38 by contacting the archwire 38 with, for example, both the first projecting portion 74, 138, or 312 or surface 232a and the second projecting portion 76, 140, 314, or surface 232b of at least one of the brackets.

In yet another embodiment, the method of correcting malpositioned teeth includes applying a plurality of orthodontic brackets constructed according to at least one of the orthodontic brackets 30, 100, 200, and 302 to teeth of a patient, and retaining an archwire 38 in the respective archwire slot 40 of the orthodontic brackets 30, 100, 200, 302 with the closure member 36, clip 106, clip 204, or member 300, for example, in the closed positions such that the archwire 38 contacts at least one of the projecting portions 74, 76, 138, 140, 312, 314 and without contacting a surface 86, 146, 330 in the recessed area 78, 136, 316 respectively.

In yet another embodiment, the surfaces 86, 146, 330 in the recessed areas 78, 136, 316 and the projecting portions 74, 76; 138, 140; or 312, 314 of the closure member 36, clip 106 or 204, or member 300, respectively, define respective curves, and the respective curves each have a radius of curvature less than a radius of curvature of the portion of the archwire retained in the associated bracket. In addition, retaining the archwire 38 may further include contacting the archwire 38 with both the mesial end 50 and the distal end 52 of at least one of the brackets, such as the mesial end 50 or the distal end 52 of the base surface 54 of the archwire slot.

While the present invention has been illustrated by a description of various embodiments and while these embodiments have been described in some detail, it is not the intention of the Applicants to restrict or in any way limit the scope of the appended claims to such detail. Additional advantages and modifications will readily appear to those of ordinary skill in the art. The various features discussed herein may be used alone or in any combination depending on the needs and preferences of the user. This has been a description of illustrative aspects and embodiments of the present invention, along with the methods of practicing the present invention as currently known. However, the invention itself should only be defined by the appended claims.

What is claimed is:

1. An orthodontic bracket for coupling an archwire with a tooth comprising:
   a bracket body adapted to be secured to the tooth and including an archwire slot having a base surface and a pair of opposed side walls extending from the base surface adapted to receive the archwire therein, and
   a slide member slidable between an open position and a closed position, being coupled to the bracket body in the closed position to retain the archwire in the archwire slot, and including a side with archwire control structure including first and second projecting portions spaced apart in a mesial-distal direction and a recessed area between the first and second projecting portions, the recessed area extending outside of the archwire slot and the projecting portions extending toward the archwire slot,
   wherein, when the slide member is in the closed position, the first and second projecting portions are spaced apart and overlie the archwire slot wherein the first and second projecting portions are adapted to contact the archwire so as to provide consistent points of contact between the archwire and the slide member to thereby produce a substantially consistent moment arm between the archwire and the bracket during orthodontic treatment, and wherein the first and second projecting portions have an asymmetric configuration relative to a longitudinal axis of the slide member so as to be unequally spaced relative to the mesial-distal dimension of the archwire slot and the first projecting portion has a width that is different than a width of the second projecting portion.

2. The orthodontic bracket of claim 1 wherein, when the orthodontic bracket is mounted to a labial surface of a tooth the opposed side walls include a gingival side wall and an occlusal side wall, the recessed area further comprises one of a gingival side wall and an occlusal side wall that together with the first and second projecting portions define a surface that is recessed in a labial direction from a lingual surface of the slide member, and where the gingival side wall of the recessed area resides in a plane of or is positioned gingivally of the gingival side wall of the archwire slot or the occlusal side wall of the archwire slot when the slide member is in the closed position.

3. The orthodontic bracket of claim 1, wherein the recessed area comprises a recessed surface in the form of a uniform arc curved in a mesial-distal direction.

4. The orthodontic bracket of claim 1 wherein, when the orthodontic bracket is mounted to a labial surface of a tooth, the projecting portions each reside in a plane of a lingual side of the slide member.

5. The orthodontic bracket of claim 1 wherein, when the orthodontic bracket is mounted to a labial surface of a tooth, the recessed area extends occlusally of an occlusal side wall of the archwire slot and gingivally of a gingival side wall of the archwire slot.

6. The orthodontic bracket of claim 1 where in each of the first and second projecting portions extends from one opposed side wall of the archwire slot to the other opposed side wall of the archwire slot.

7. The orthodontic bracket of claim 1, wherein a first distance from a mesial end of the archwire slot to the second projecting portion is different than a second distance from a distal end of the archwire slot to the first projecting portion.

8. A method of correcting malpositioned teeth, comprising:
applying a plurality of orthodontic brackets to teeth of a patient, each bracket comprising:
   a bracket body including a mesial end, a distal end, a lingual side, a labial side, and an archwire slot extending generally from the mesial end to the distal end, the archwire slot including a base surface and an occlusal side wall and a gingival side wall, the occlusal side wall and the gingival side wall extending in a labial direction from the base surface, the archwire slot further including an opening on the labial side opposite the base surface for receiving an archwire, and
   a slide member slidably coupled to the bracket body between an opened position and a closed position, the slide member configured to retain the archwire in the archwire slot in the closed position, the slide member including a lingual side with archwire control structure including first and second projecting portions spaced apart in a mesial-distal direction and a recessed area between the first and second projecting portions, the recessed area extending outside of the archwire slot and the projecting portions extending toward the archwire slot,
   wherein, when the slide member is in the closed position, the first and second projecting portions overlie the archwire slot with the first projecting portion proximate the mesial end of the archwire slot and the second projecting portion proximate the distal end of the archwire slot, wherein at least one of the first or second projecting portions is adapted to contact the archwire when the slide member is coupled to the bracket body, and wherein the first and second projecting portions have an asymmetric configuration relative to a longitudinal axis of the slide member so as to be unequally spaced relative to the mesial-distal dimension of the archwire slot and the first projecting portion having a width that is different than a width of the second projecting portion; and
retaining an archwire in the respective archwire slots of the orthodontic brackets such that the archwire contacts at least one of the first or second projecting portions and without contacting another portion of the slide member to thereby provide consistent points of contact between the archwire and the slide member to produce a substantially consistent moment arm between the archwire and the bracket during orthodontic treatment.

9. The method of claim 8, wherein the first and second projecting portions of each slide member define respective surfaces, and the respective surfaces each have a radius of curvature less than a radius of curvature of the portion of the archwire retained in the associated bracket.

10. An orthodontic bracket comprising: a bracket body adapted to be secured to a tooth and including an archwire slot configured for receiving an archwire, and a slide member slidable between an open position and a closed position and being configured to retain the archwire in the archwire slot when in the closed position, the slide member including a side with archwire control structure including a first and second projecting portions spaced apart by a fixed mesial-distal distance in a plane of the side of the slide member and a recessed area between the first and second projecting portions, the recessed area extending outside of the archwire slot, wherein, when the slide member is in the closed position, the recessed area, the first projecting portion, and the second projecting portion overlie the archwire slot, wherein when the archwire is in contact with one or both of the first and second projecting portions, the recessed area is configured to allow an apex of a bend in the archwire to extend into the recessed area without contacting another portion of the slide member within the recessed area, and wherein the first and second projecting portions are unequally spaced relative to the mesial-distal dimension of the archwire slot and the first projecting portion having a width that is different than a width of the second projecting portion.

11. The orthodontic bracket of claim 10 wherein a depth of the recessed area is greater than the distance to which the apex of the archwire extends into the recessed area.

* * * * *

UNITED STATES PATENT AND TRADEMARK OFFICE
CERTIFICATE OF CORRECTION

| | | |
|---|---|---|
| PATENT NO. | : 9,004,916 B2 | |
| APPLICATION NO. | : 12/689145 | |
| DATED | : April 14, 2015 | |
| INVENTOR(S) | : Albert Ruiz-Vela et al. | |

It is certified that error appears in the above-identified patent and that said Letters Patent is hereby corrected as shown below:

In the claims,

At column 20, claim number 10, line number 32, after "including" delete "a"

Signed and Sealed this
Ninth Day of February, 2016

Michelle K. Lee
*Director of the United States Patent and Trademark Office*